(12) United States Patent
Lo et al.

(10) Patent No.: US 7,559,899 B2
(45) Date of Patent: Jul. 14, 2009

(54) POWER SAVING TECHNIQUES FOR CONTINUOUS HEART RATE MONITORING

(75) Inventors: Thomas Ying-Ching Lo, Fremont, CA (US); Karthik H. Katingari, Milpitas, CA (US)

(73) Assignee: Salutron, Inc., Fremont, CA (US)

( * ) Notice: Subject to any disclaimer, the term of this patent is extended or adjusted under 35 U.S.C. 154(b) by 407 days.

(21) Appl. No.: 11/402,476

(22) Filed: Apr. 12, 2006

(65) Prior Publication Data

US 2007/0244398 A1    Oct. 18, 2007

(51) Int. Cl.
*A61B 5/02*   (2006.01)
(52) U.S. Cl. ............... 600/502; 600/500; 600/481
(58) Field of Classification Search ............ 600/481, 600/500–507
See application file for complete search history.

(56) References Cited

U.S. PATENT DOCUMENTS

| | | | |
|---|---|---|---|
| 5,738,104 A | | 4/1998 | Lo et al. |
| 5,746,697 A | * | 5/1998 | Swedlow et al. ............ 600/323 |
| 5,876,350 A | | 3/1999 | Lo et al. |
| 5,924,979 A | * | 7/1999 | Swedlow et al. ............ 600/300 |
| 6,579,242 B2 | * | 6/2003 | Bui et al. .................... 600/537 |
| 6,758,816 B1 | | 7/2004 | Tsubata et al. |
| 6,863,652 B2 | * | 3/2005 | Huang et al. ................ 600/300 |
| 2002/0065454 A1 | * | 5/2002 | Lebel et al. ................. 600/365 |
| 2003/0065269 A1 | * | 4/2003 | Vetter et al. ................. 600/503 |
| 2004/0260191 A1 | | 12/2004 | Stubbs |
| 2006/0253010 A1 | * | 11/2006 | Brady et al. ................. 600/324 |
| 2007/0038049 A1 | * | 2/2007 | Huang ......................... 600/323 |

OTHER PUBLICATIONS

International Search Report and Written Opinion of the International Searching Authority, dated Aug. 12, 2008, PCT Appl. No. PCT/US07/07769.

* cited by examiner

*Primary Examiner*—Karen E. Toth
(74) *Attorney, Agent, or Firm*—Vierra Magen Marcus & DeNiro LLP

(57) ABSTRACT

A heart rate monitor implements power saving algorithms while monitoring a subject's heart rate. The monitor continuously monitors a subject during an initial period to determine an initial heart rate. After the initial heart rate is acquired, power may not be provided for portions of the monitor until a heart beat is expected to occur. At some point before the expected heart beat occurs, power is returned to the components which have not received power. The expected heart beat is then detected, and power to selected portions of the monitor is terminated again until another expected heart beat approaches in time. By providing power to monitor components just before an expected heart beat, the monitor may still detect the heart beat and determine the corresponding heart rate of the user. The period of time during which power is terminated for some components may be determined from the detected heart rate. The number of heart beats during which power is terminated for selected monitor components may vary.

25 Claims, 20 Drawing Sheets

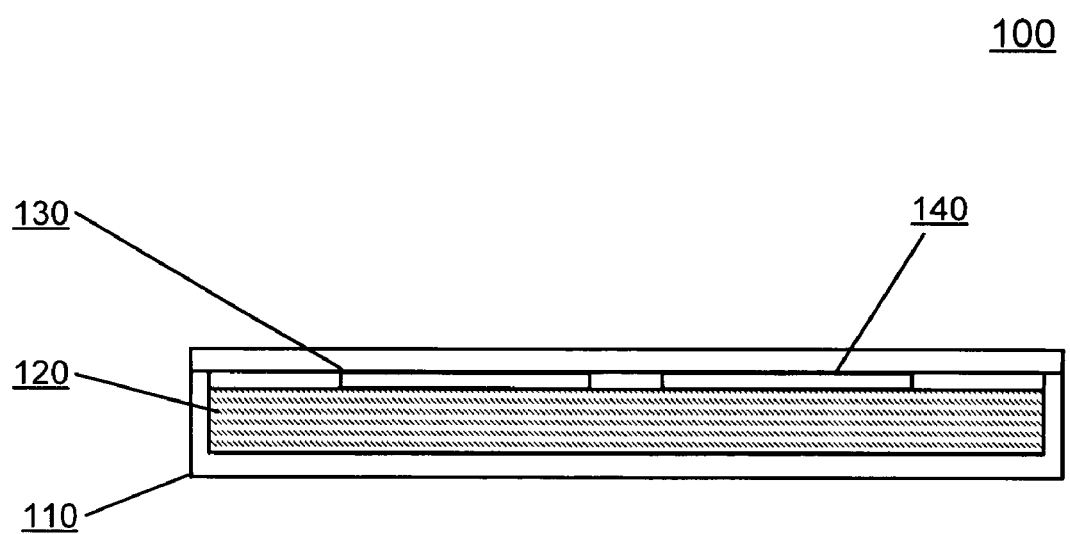
Figure 1 – Prior Art

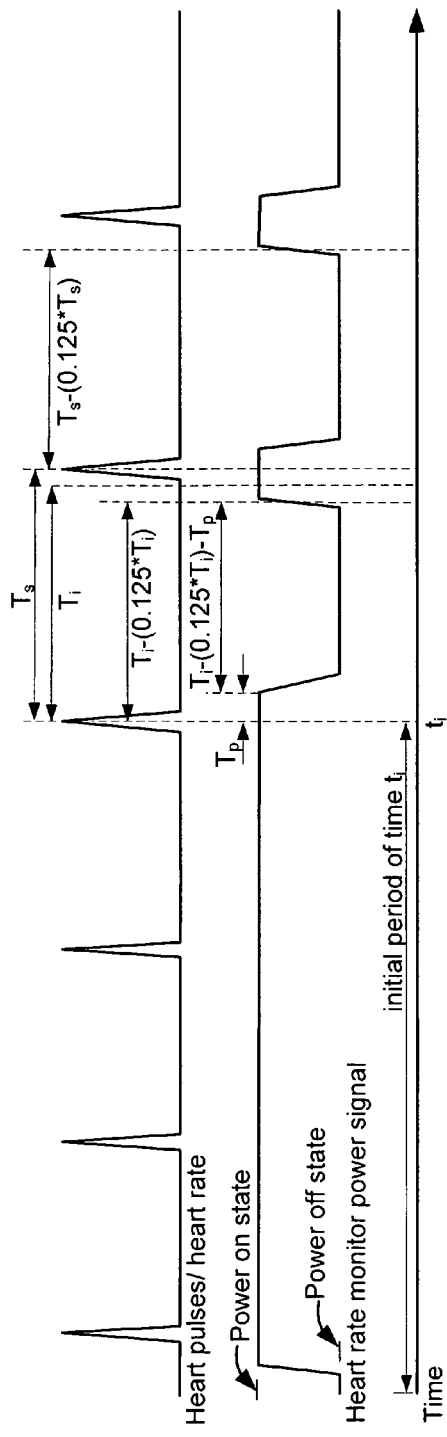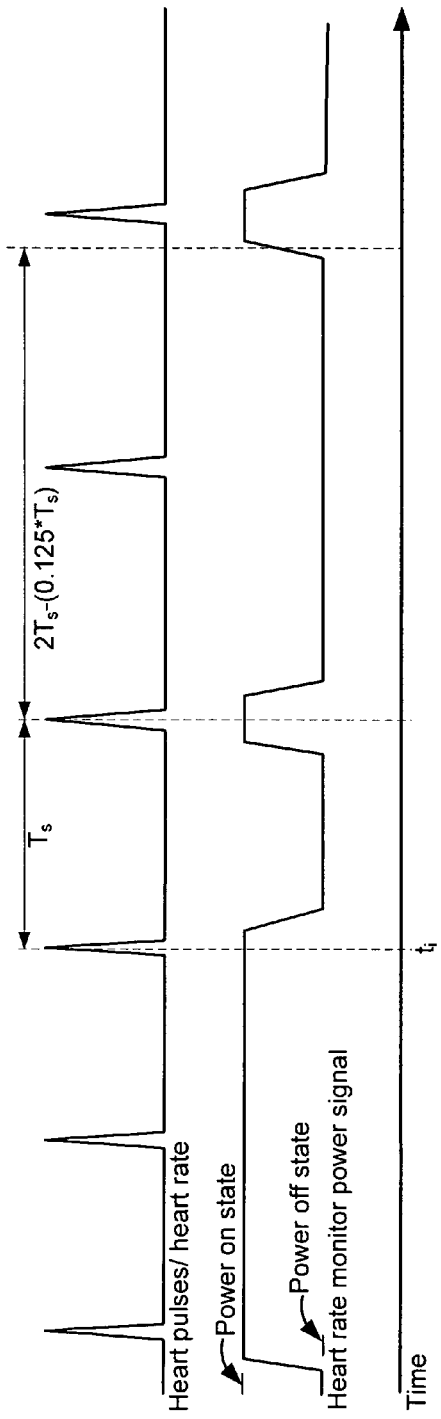

POWER SAVING TECHNIQUES FOR CONTINUOUS HEART RATE MONITORING

BACKGROUND

Measuring heart and pulse rates in living subjects has become a valuable tool during physical exercise and for health monitoring. The heart rate and pulse rate of a subject are related. Heart rate may be defined as the number of heart contractions over a specific time period, usually defined in beats per minute. A pulse is defined as the rhythmical dilation of a blood vessel produced by the increased volume of blood forced through the vessel by the contraction of the heart. Since heart contractions normally produce a volume of blood that can be measured as a pulse, heart rate and pulse rate are ideally the same. However, a pulse or pulse rate may differ from the heart rate during irregular heart beats or premature heart beats. In this case, a heart contraction may not force enough blood through a blood vessel to be measured as a pulse.

A pulse rate is measured by counting the rate of pulsation of a subject's artery. The heart rate is measured by sensing the electrical activity of the heart based on electrocardiograms (for example EKG or ECG). Heart and pulse rates may be monitored for a variety of reasons. Individuals who want to increase their endurance or performance may wish to exercise while maintaining target heart rates. Conversely, subjects with a history of heart disease or other heart related condition should avoid exceeding a certain heart or pulse rate to reduce unnecessary strain on their heart.

Pulse rate can be measured at the wrist. The shallow depth of the radial artery in the wrist offers a number of advantages for achieving continuous pulse detection at the wrist. However, some prior wrist-based monitors have disadvantages. For example, prior sensors that monitor pressure pulses in the wrist have not been effective. Pressure pulses are attenuated by the tissues between the artery and the sensor. Most of the high frequency signal components are lost because of the attenuation. Additionally, muscle movement may create substantial low frequency noise at the pressure sensors. The low frequency noise signals make reliable identification of low frequency blood pressure pulses very difficult.

Ultrasonic monitors using sonar technology were developed to overcome low frequency noise signal problems. Ultrasonic monitors transmit ultrasonic energy as a pulse signal. When a power source drives a transducer element, such as a piezoelectric crystal, to generate the pulse signal, the ultrasonic pulse signal is generated in all directions, including the direction of the object to be measured (such as a blood vessel). The portion of the ultrasonic pulse signal reaching the vessel is then reflected by the vessel. When the blood vessel experiences movement, such as an expansion due to blood flow from a heart contraction, the reflected pulse signal experiences a frequency shift, also known as the Doppler shift.

When either the source of a sonar or ultrasonic signal or the observer of the signal is in motion, an apparent shift in frequency results. The shift in frequency is known as the Doppler effect. If R is the distance from the ultrasonic monitor to the blood vessel, the total number of wavelengths $\lambda$ contained in the two-way path between the ultrasonic monitor and the target is $2R/\lambda$. The distance R and the wavelength $\lambda$ are assumed to be measured in the same units. Since one wavelength corresponds to an angular excursion of $2\pi$ radians, the total angular excursion $\Phi$ made by the ultrasound wave during its transit to and from the blood vessel is $4\pi R/\lambda$ radians. When the blood vessel experiences movement, R and the phase $\Phi$ are continually changing. A change in $\Phi$ with respect to time is equal to a frequency. This is the Doppler angular frequency $W_d$, given by $$W_d = 2\pi f_d = \frac{d\Phi}{dt} = \frac{4\pi}{\lambda}\frac{dR}{dt} = \frac{4\pi V_r}{\lambda}$$

where $f_d$ is the Doppler frequency shift and $V_r$ is the relative (or radial) velocity of target with respect to the ultrasonic monitor.

The amount of the frequency shift is thus related to the speed of the moving object from which the signal reflects. Thus, for heart rate monitor applications, the flow rate or flow velocity of blood through a blood vessel is related to the amount of Doppler shift in the reflected signal.

A piezoelectric crystal may be used in a monitor both as the power generator and the signal detector. In this case, the ultrasonic energy is emitted in a pulsed mode. The reflected signal is then received by the same crystal after the output power source is turned off. The time required to receive the reflected signal depends upon the distance between the source and the object. Using a single crystal to measure heart rates requires high speed power switching due to the short distance between source and object. In addition, muscle movement generates noise that compromise the signal-to-noise-ratio in the system. The muscle movement noise has a frequency range similar to the frequency shift detected from blood vessel wall motion. Therefore, it is very difficult to determine heart rates with this method.

In some ultrasonic signal systems, two piezoelectric elements are used to continuously measure a pulse. The two elements can be positioned on a base plate at an angle to the direction of the blood flow. In continuous pulse rate measurement, the Doppler shift due to blood flow has a higher frequency than the shifts due to muscle artifacts or tissue movement. Therefore, even if the muscle motion induced signals have larger amplitudes, they can be removed by a high pass filter to retain the higher frequency blood flow signals. The disadvantages of continuous mode over pulsed mode are higher cost and more power consumption In addition to ultrasound, other technologies have been used to monitor a subject's heart rate or pulse rate. These technologies include EKG, oximeters, radio frequency, and laser. Each of these technologies has its own disadvantages in measuring heart rates and pulse rates.

EKG signals are commonly used in medical environments to diagnose heart diseases and to calculate a patient's heart rate. To implement EKC technology, EKG electrodes are usually placed on patient's chest or limbs. Once placed, the electrodes communicate data to a processing device. The processing device may be a stand-alone machine, a wrist worn device, or some other device. The disadvantage with EKG technology is that it is used with a chest strap to monitor the subject's heart. It is not practical for use in a wrist worn device without a chest strap.

Oximeters which monitor oxygen content in a subject's blood can provide heart rate information as a byproduct. An oximeter directs infrared light or laser light at a subject's blood vessel. A monitor device then determines the amount of light absorption (or transmission of light energy) by the subject's blood. The change of light intensity with respect to time is used to compute the heart rate. The light emitter and detector is usually wrapped around a finger tip or clamped on an earlobe where arteries or arterioles can be found superficially.

Radio frequency (RF) technology uses the same Doppler principles as ultrasound-based heart rate monitors. Unlike ultrasound monitors, an RF signal transmitter and receiver do not need to have direct contact with the subject in order to efficiently send and receive signals to a subject. However, an RF-based monitor uses a Doppler signal with a much narrower band than ultrasound monitors. As a result, RF technology is not practical for wrist worn heart rate monitors used in the sports and fitness industry Laser Doppler devices can be used to detect a heart rate based on the same Doppler principle used in ultrasound devices. However, the cost for using laser technology to monitor heart rates is very high. Also, the bandwidth used by laser devices is narrow, and therefore not practical for every day sports and fitness use.

For medical or industrial use where power consumption is not an issue, EKG, oximeter, radio frequency, and laser technologies can be applied to the subject to obtain continuous heart rate readings. However, for the portable, wearable and battery driven heart rate monitors which are popular in sports and fitness use, some of the above technologies are not practical.

For example, EKG based heart rate monitors are widely used for sports and fitness applications. This widespread use of EKG technology is because an EKG electrode is a passive device that requires no power. The only power consumption in an EKG based monitor is in the electronic circuit that processes the EKG signals received from the heart. Therefore, a standard lithium coin battery is suitable for use in these devices. This technology, however, requires the use of a chest strap to achieve continuous monitoring.

Other technologies, including the oximeter, radio frequency, and laser technologies mentioned above, require power to drive transmitting and receiving components. The power is required regardless of where the transducers are placed on the body (e.g., finger tip, earlobe, temple, neck, wrist, or other body location where blood pulse can be found fairly easily). For heart rate monitors using these technologies, it is desirable to reduce the power consumption of the device.

SUMMARY

The present technology, roughly described, pertains to reducing the power consumption in heart rate monitors. Heart rate monitor uses signals to measure movement inside the body of a living subject. The movement may be a heart contraction, flowing blood or movement of the blood vessel itself. From information collected from these movements, electronics within the monitor may determine blood flow rate, heart rate, or pulse rate of the living subject.

Power saving techniques can be used during different periods of heart or pulse rate monitoring. In one embodiment, the heart rate monitor continuously monitors a subject during an initial period to determine an initial heart rate. During the initial period, power is provided to a signal transmitter, signal receiver and signal processing circuitry without interruption. After the initial heart rate is acquired, power may be terminated or reduced for portions of the monitor until a heart beat is expected to occur. At some point before the expected heart beat occurs, full power is returned to the components and circuitry which may not have been full receiving power. A heart beat is then detected, and power is terminated or reduced for selected portions of the monitor until another expected heart beat approaches in time.

In one embodiment, the power is terminated or reduced to selected components of a monitor for a pre-determined period of time. The period may be determined based on the detected heart rate. For example, once the initial heart rate is determined, the time period between consecutive heart beats can be calculated as the inverse of the heart rate. Thus, after determining the initial heart rate, the monitor may terminate the power supplied to selected monitor components for a period which ends just before a heart beat is expected to occur. By providing power to monitor components just before an expected heart beat, the monitor may reduce power consumption but still detect the heart beat and determine the corresponding heart rate of the user. In one embodiment, power may be returned to portions of the monitor at times to ensure that heart beats associated with a changing heart rate can be detected.

In some embodiments, the number of heart beats during which power is terminated or reduced may vary. In some cases, after the initial period, the monitor may terminate or reduce the power provided to selected components until the very next heart beat. In other cases, the monitor terminates or reduces power for selected components until the second, third or a later heart beat is expected to occur, thereby skipping one or more heart beats.

The power saving techniques discussed herein may be used with any number of different technologies. For example, the present power saving techniques may be used in monitors that use ultrasound, infrared, pressure sensing, radio frequency, and/or laser technology.

This summary introduces a selection of simplified concepts that are further described below in the description. This summary is not intended to identify key features or essential features of the claimed subject matter, nor is it intended to be used as an aid in determining the scope of the claimed subject matter.

BRIEF DESCRIPTION OF THE DRAWINGS

FIG. 1 illustrates a cross section of an monitor of the prior art.

FIG. 5D illustrates an example of a heart rate monitor power signal over time.

FIG. 5E illustrates another example of a heart rate monitor power signal over time.

DETAILED DESCRIPTION

Figure 2A:
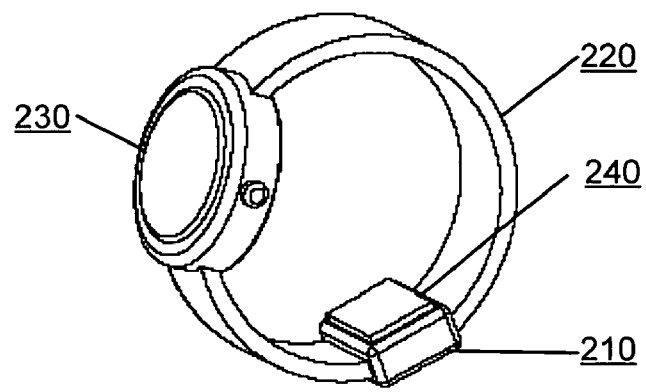
FIG. 2A illustrates one embodiment of an monitor with a physical connection to a display device.

The present technology pertains to a heart rate monitor. The monitor utilizes transmitted signals to measure movement inside the body of a living subject. The movement may be a heart contraction, flowing blood or movement of the blood vessel itself. From information collected from these movements, electronics within the monitor may determine blood flow rate, heart rate, or pulse rate of the living subject.

In one embodiment, the monitor measures blood flow through an artery of a person. The monitor transmits signals which are reflected by blood vessel motion. The blood vessel motion may be vessel expansion or blood flowing through the blood vessel. Signals reflected from blood vessel expansion (expansion due to blood moving through the vessel) have a frequency range similar to that of noise caused by muscle artifacts and tissue movement. The signals reflected by the flowing blood itself have a frequency range higher than muscle and tissue related noise. As a result, the signals reflected by flowing blood are easier to process to find heart and/or pulse rates than those reflected by expansion of the blood vessel itself.

The heart rate monitor may implement power saving algorithms while monitoring a subjects heart rate. While implementing the power saving algorithms, the monitor may terminate and/or reduce power to selected monitor components at different periods of time. In some embodiments, the selected monitor components may receive full power only during a time window associated with an expected heart beat or pulse. As a result, the monitor may accurately detect the heart rate or pulse of a user while reducing power consumption. Though embodiments may be discussed below with respect to terminating power, it is intended that power may be reduced rather than completely terminating the power in embodiments discussed herein.

Determining the heart rate of a user may begin with continuously monitoring a subject during an initial period. The subject is continuously monitored during the initial period to determine an initial heart rate. In one embodiment, during the initial period, power is provided to a signal transmitter, signal receiver and signal processing circuitry without interruption. After the initial heart rate is acquired, power may be terminated for portions of the monitor until just before a heart beat is expected to occur. At some point before the expected heart beat occurs, power is provided to the monitor components (signal transmitter, signal receiver, signal processing circuitry and/or any other circuitry) to which power was terminated earlier. The expected heart beat is then detected, and power is shut down to selected portions of the monitor until another expected heart beat approaches in time.

In one embodiment, power is not provided to selected components of a monitor for a pre-determined period of time. The period of time may be determined based on the detected heart rate. For example, once the initial heart rate is determined, the time period between consecutive heart beats can be calculated as the inverse of the initial heart rate. Thus, after determining the initial heart rate, the monitor may terminate power to selected monitor components for a period which ends just before a heart beat is expected to occur. By providing power to monitor components just before an expected heart beat, the monitor may still detect the heart beat and determine the corresponding heart rate of the user. In one embodiment, the time window during which the monitor returns power may be adjusted to ensure that heart beats associated with a changing heart rate (for example, beats that occur before or after the expected time) can be detected.

In some embodiments, the number of heart beats during which power is terminated for selected monitor components may vary. In some cases, after the initial period, the monitor may terminate power for selected components for a period of time which expires just before the very next heart beat. In other cases, the monitor may terminate power for selected components until the second, third or a later heart beat is expected to occur. This is discussed in more detail below.

The power saving techniques discussed herein may be used with any number of different technologies. For example, the present power saving techniques may be used in monitors that utilize ultrasound, infrared, pressure sensing, radio frequency, and/or laser technology. In some cases below, the monitor discussed will be referred to as an ultrasonic monitor. This is done for discussion purposes only, and it will be understood that monitors which utilize other technologies may be used as the monitor discussed herein as well. Additionally, a monitor as discussed below may be referred to as heart rate monitor or a pulse monitor. Reference to either monitor type is not intended to be exclusive to the other, and the two monitors are intended to be used interchangeable in the embodiments discussed herein.

Figure 2B:
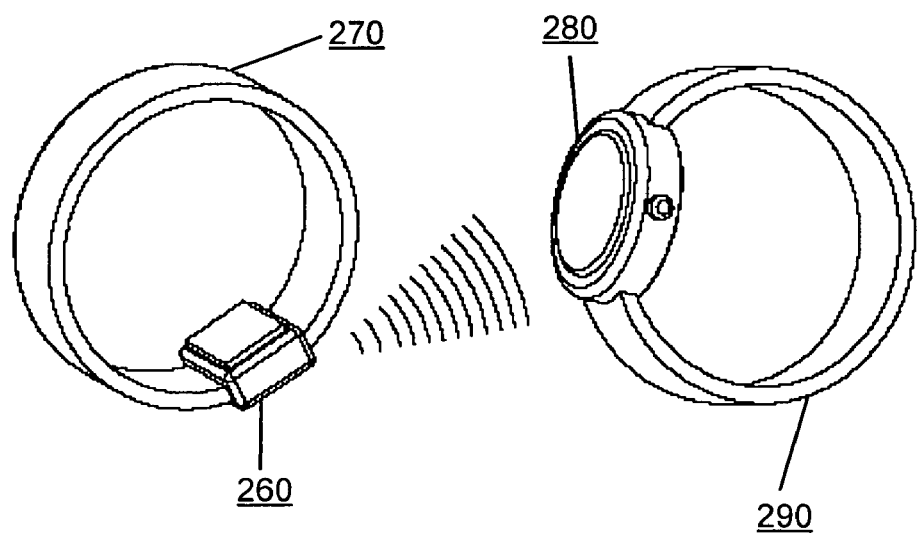
FIG. 2B illustrates one embodiment of an monitor with a wireless connection to a display device.
Figure 3:
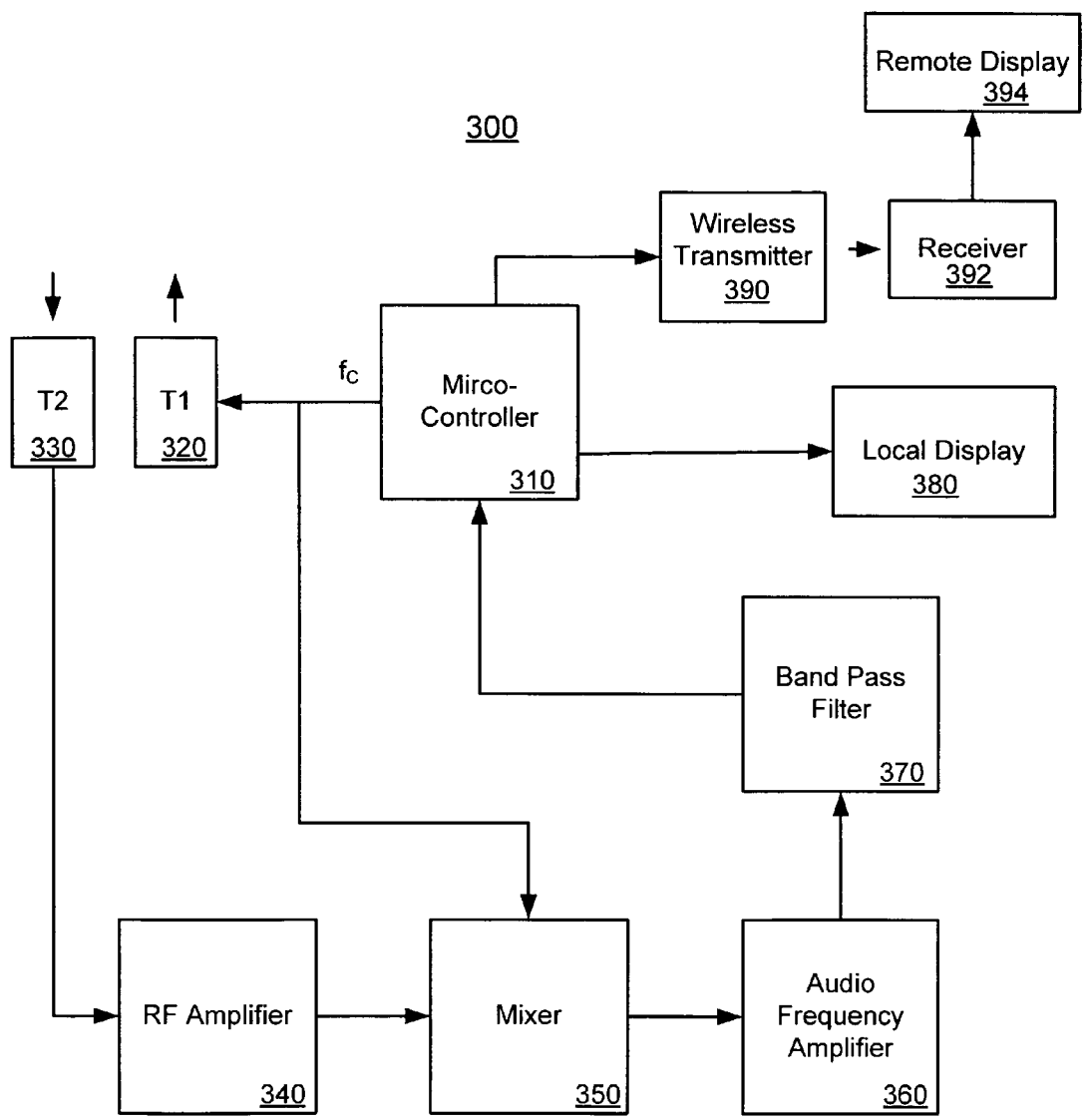
FIG. 3 illustrates one embodiment of a block diagram of an ultrasonic monitor.
Figure 4A:
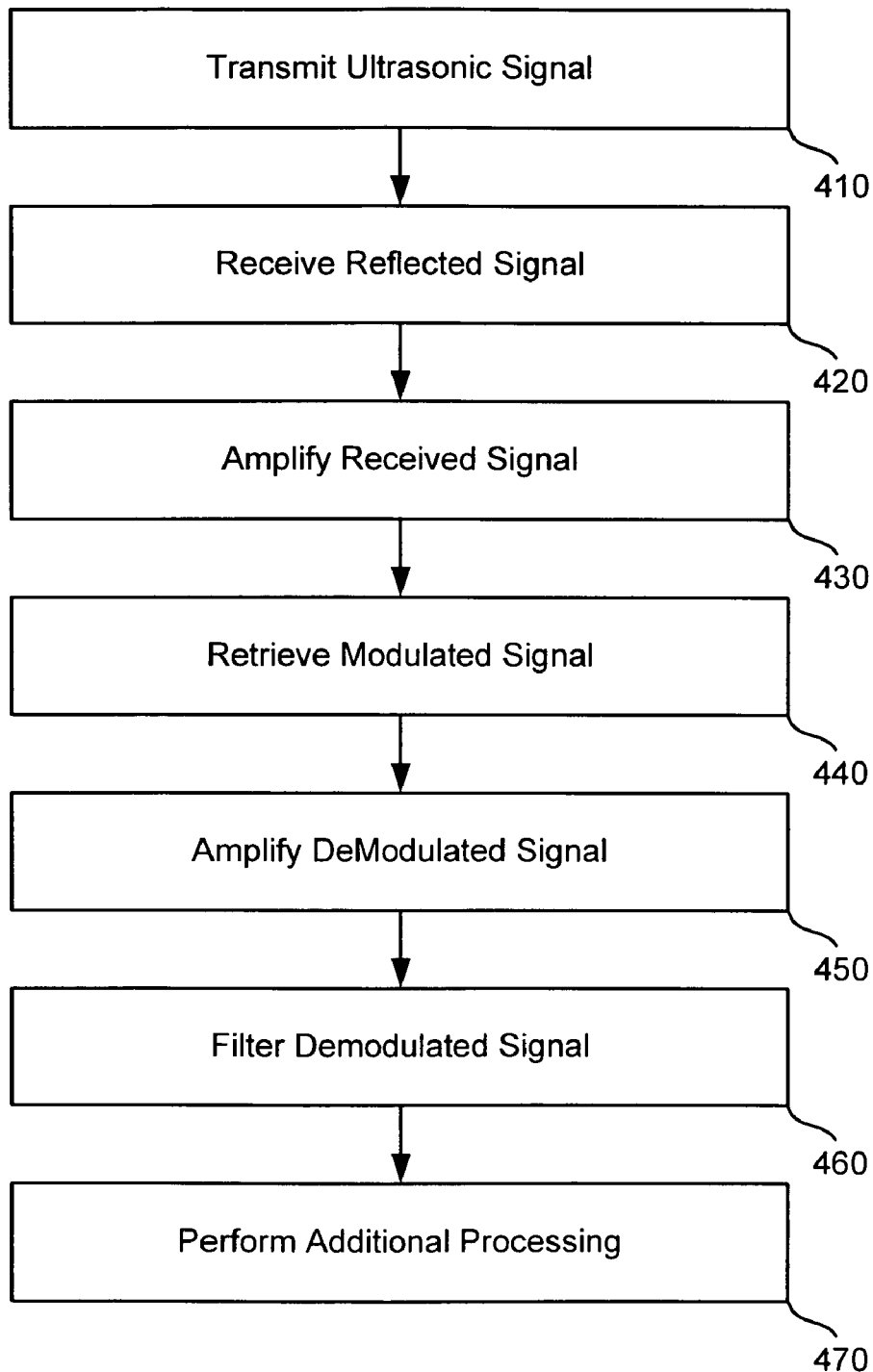
FIG. 4A illustrates a flowchart of an embodiment of a method of operation of an ultrasonic monitor.
Figure 4B:
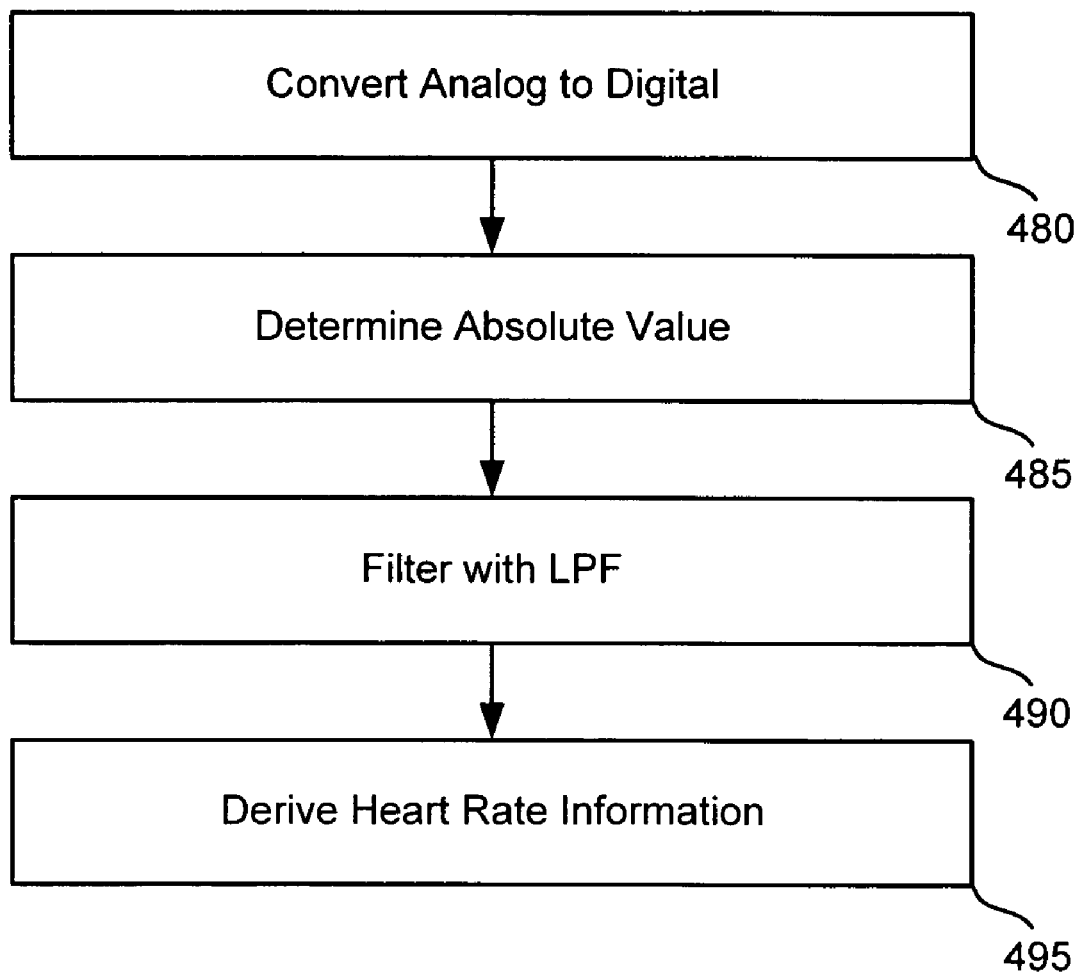
FIG. 4B illustrates a flowchart of an embodiment of a method for performing additional processing by an ultrasonic monitor.

The discussion below proceeds as follows. FIGS. 2A-3 provide information regarding a heart rate monitor system. FIGS. 4A-4B provide information regarding operation of a heart rate monitoring system of the present technology. FIGS. 5A-5E provide information regarding implementation of power saving methods for determining a heart rate. FIGS. 6-9C provide information on implementing a heart rate monitor using a printed circuit board (PCB). FIG. 10A provides information for using a gel pad with a heart rate monitor, and FIGS. 10B-C provide information regarding use of an adhesive member with a heart rate monitor. FIGS. 11A-15B provide information associated with other embodiments of the present technology.

Embodiments of a heart rate monitor discussed herein may include a gel pad, an oil based transition medium, an adhesive member, and other features. In addition to the embodiments discussed below, these embodiments are described in the following patent and patent applications, all of which are hereby incorporated by reference in their entirety: U.S. Pat. No. 6,843,771, issued on Jan. 18, 2005, entitled "ULTRASONIC MONITOR FOR MEASURING HEART RATE AND BLOOD FLOW RATE," having inventors Thomas Ying-Ching Lo and Tolentino Escorcio; U.S. patent application Ser. No. 10/990,794, filed on Nov. 17, 2004, entitled "ULTRASONIC MONITOR FOR MEASURING BLOOD FLOW AND PULSE RATES", having inventor Thomas Ying-Ching Lo and Rong Jong Chang; U.S. patent application Ser. No. 10/991,115, filed on Nov. 17, 2004, entitled "GEL PAD FOR USE WITH AN ULTRASONIC MONITOR", having inventors Thomas Ying-Ching Lo and Rong Jong Chang; U.S. patent application Ser. No. 11/124,707, filed on May 9, 2005, entitled "AN ULTRASONIC MONITOR WITH A BIOCOMPATIBLE OIL BASED TRANSMISSION MEDIUM", having inventors Thomas Ying-Ching Lo and Rong Jong Chang; and U.S. patent application Ser. No. 11/148,144, filed on Jun. 8, 2005, entitled "AN ULTRASONIC MONITOR WITH AN ADHESIVE MEMBER," having inventors Thomas Ying-Ching Lo and Rong Jong Chang.

As discussed above, the technology discussed herein may be used with a variety of technologies. One suitable technology is ultrasound technology. The terms ultrasonic and ultrasound are used interchangeably herein and refer to a sound wave having a frequency between about 30 KHz and about 30 MHz. An ultrasonic transducer, or transducer element, as used herein is a device used to introduce sonic energy into and detect reflected signals from a living subject. Ultrasonic transducers respond to electric pulses from a driving device and ultrasonic pulses reflected by a subject.

A heart rate monitor is comprised of an electronics portion and a transmission portion. The electronics portion includes the electrical components required to transmit, receive, and process the ultrasonic signals as discussed with respect to FIGS. 3-5. Processing may include amplifying, filtering, demodulating, digitizing, squaring, and other functions, including typically signal processing functions. Processing may be performed all or in part by digital circuitry. For example, the received ultrasonic signal can be digitized. The processing described herein to the received signal can then be performed by digital circuitry. The transmission portion, or transmission medium, may include a biocompatible oil-based transmission medium, gel pad, an adhesive member, or combination of these between the monitor and the subject. In some embodiments, the adhesive member can be positioned in direct contact with the living subject and the ultrasonic monitor. In some embodiments, the adhesive member is in contact with the gel pad, and the adhesive member and gel pad provide transmission of ultrasonic signals between an ultrasonic monitor and a subject. Adhesive members, oil based transmission mediums and gel pads are discussed in more detail below.

FIG. 2A illustrates an embodiment of a wrist worn monitor system 200. System 200 includes a monitor module 210, a strap 220, a display device 230 and a transmission medium 240. Monitor module 210 detects blood flow through the radial artery at the subject's wrist. Heart rate data is then provided directly to display module 230. In one embodiment, connecting wires are molded into strap 220 between the monitor module 210 and display device 230.

The monitor can also be implemented with a remote display. Monitor system 250 of FIG. 2B includes monitor module 260, first strap 270 attached to monitor module 260, remote display module 280 and second strap 290 attached to remote display module 280. Monitor module 260 detects the blood flow through a radial artery in the subject's wrist. Heart rate data is derived from the detected blood flow and provided to remote display module 280. Monitor 260 can wirelessly transmit information to remote display 280 using a wireless transmitter (not shown). The remote display 260 includes a receiver (not shown) to receive the transmission from monitor 260. The remote display 280 may be a monitor screen or other device. Remote display module 280 may be attached to a part of the subject's body (such as the chest over the subject's heart) with a biocompatible adhesive or a transmission medium.

The monitor of the present technology may be configured to suit a particular application. Examples of configurable monitor elements include signal frequency and transducer size. Determining what signal frequency to use may depend on the particular object being monitored and the technology being used. The wrist offers a convenient location for positioning the monitoring device. In some embodiments, the relatively shallow focal depth of the radial artery in the wrist is compatible with a high frequency carrier signal.

The size of the transducer or other transmitting elements also affects the signal frequency. With respect to ultrasound devices, thinner electromechanical resonators emit at higher frequencies. Transducer elements driven by high frequency signals tend to vibrate more rapidly and consume more power than those operating at lower frequencies. This is primarily due to internal loss. The monitor amplifier and demodulation circuits will also consume more power processing the higher frequencies.

In one embodiment, with respect to ultrasound monitors, the transducers used in the present technology adhere to some general design guidelines. The transducers of the ultrasonic monitors can be piezoelectronic transducers. The length of each transducer is generally about one centimeter long. The transducer length is also generally equal or greater than five times its width. The frequency at which a transducer operates at is generally related to the thickness of the transducer. Several types of transducers may be used in the present invention. One example is a K-350, Modified Lead Zirconate-Titanate transducer, by Keramos Division, Piezo Technologies. Equivalent materials to this type of transducer include PZT-5A or NAVY-II equivalent.

A block diagram of one embodiment of a monitor system 300 is illustrated in FIG. 3. Monitor system 300 includes a microcontroller 310, a transmitting transducer element 320 connected to microcontroller 310, a receiving transducer element 330, a radio frequency (RF) amplifier 340 connected to receiving transducer 330, a mixer 350 connected to RF amplifier 340 and microcontroller 310, an audio amplifier 360 connected to mixer 350, and band pass (BP) filter 370 connected to audio frequency amplifier 360 and microcontroller 310. Monitor system 300 may optionally include a local display 380 connected to microcontroller 310, a wireless transmitter 390 connected to microcontroller 310, a wireless receiver 392 receiving a wireless signal from wireless transmitter 390, and a remote display 394 connected to receiver 392.

Microcontroller 310 of the monitor can be implemented as one or more of several common microcontroller integrated circuits, including Samsung KS57C 3316 series, Samsung S3C7335, Intel 8051 series, and Texas Instruments MSP430 series microcontrollers. Mixer 350 of the monitor can be implemented as one or more of several common mixer ICs or frequency modulation ICs. A non-exclusive list of possible mixer ICs include NJC's NJM2295, NJM2292 and NJM2537 mixers, Toko's TK8336IM mixer, and Motorola's MC3371 mixer.

In one embodiment, a monitor can be implemented with a system similar to that represented by block diagram 300, but with a driver circuit and high pass and low pass filters. In this case, microcontroller 310 drives driver circuitry with a carrier signal. The driver circuitry drives transmitting transducer 320 to transmit a signal at the carrier frequency. The signal is reflected and received by receiving transducer 330. The received signal includes a frequency shift from the signal transmitted by transmitting transducer 320. The received signal is amplified by RF amplifier circuitry 340. The amplified signal is then processed by mixer 350, which demodulates the received signal and generates a signal with an audio range frequency. The resulting signal is then amplified by audio frequency amplifier circuit 360. In one embodiment, the amplified audio signal is then filtered by a high pass filter circuit and a low pass filter circuit (collectively illustrated by band pass filter 370). The filtered signal is then received by microcontroller 310, which processes the filtered signal and provides an output signal to wireless transmitter 390. Wireless transmitter 390 transmits the signal through a wireless means to receiver 392. Remote display 394 then receives the signal from receiver 392 and displays information derived from the signal.

The flowchart of FIG. 4A illustrates the operation of one embodiment of a monitor such as that represented in FIG. 3. First, a signal is transmitted at step 410. With respect to system 300, microcontroller 310 drives a transmitting transducer element 320 with a carrier signal $f_C$. As a result, the transmitting transducer transmits or generates a signal. In one embodiment, with respect to ultrasound monitors, the carrier signal may be within a range of 30 KHz to 30 MHz. In another embodiment, the carrier signal may be within a range of 1 MHz to 10 MHz. In yet another embodiment, the carrier signal is about 5 MHz. In some embodiments, the carrier signal may have a frequency in other ranges.

A reflected signal is received at step 420. The reflected signal is generated when the transmitted signal of step 410 reflects from a blood vessel. When the monitor is worn on a wrist, the radial artery reflects the transmitted signal. The received signal will contain a carrier frequency that has experienced a Doppler shift from the signal transmitted by transmitting transducer 320. After receiving the reflected signal, the received signal is amplified at step 430. In one embodiment, the amplifier 340 of system 300 is implemented as a radio frequency amplifier. The received signal is amplified by a factor that allows the signal to be processed for demodulation. Once the signal is amplified at step 430, it is processed by mixer 350 at step 440. The mixer uses the carrier signal $f_C$ to demodulate the reflected signal in order to extract the Doppler signal. Accordingly, mixer 350 is driven by carrier signal $f_C$ and the reflected signal. The retrieved modulated output signal provided by mixer 350 is then amplified at step 450 by amplifier 360. The output of the mixer will have a frequency component in the audio range. Amplifier 360 is an audio amplifier designed to amplify the demodulated audio range Doppler frequencies. For mixer output signals having non-audio range frequencies, other circuitry may be used to process the signal.

After the demodulated signal has been amplified, the amplified signal is filtered at step 460. In one embodiment, the filter of step 460 is a band pass filter. The band pass filter may be configured to remove aliasing effects, noise, and other unwanted frequency elements. In some embodiments, the band pass filter may be implemented with a high pass and low pass filter. After the signal is filtered at step 460, the signal is subject to additional processing at step 470.

The additional processing of step 470 may include several steps depending on the monitor system. The processing may be performed by a microcontroller or other circuitry. Though methods vary, a typical example of additional processing is illustrated in the flowchart of FIG. 4B. First, the filtered signal from step 460 of the flowchart of FIG. 4A is processed by an analog to digital converter at step 480. In one embodiment, the digitization is performed if it was not performed earlier. The absolute value of the digitized signal is then determined at step 485. Alternatively, the square of the signal may be determined at step 485. Next, the signal derived at step 485 is filtered by a low pass filter at step 490. The low pass filter removes noise and other unwanted frequency elements of the signal. The heart rate is then derived from the resulting signal at step 495. After the processing of steps 480-495, the resulting signal is a pulse signal retrieved from the receiving transducer. The signal appears as a series of pulses, wherein each pulse has an area as determined by the path of its amplitude to and from a peak amplitude. The resulting heart rate, or pulse rate, is derived from the frequency of the pulses (for example, 160 pulses per minute corresponds to 160 heart beats per minute in step 540). The flow rate is determined by integrating the area underneath the waveform of the pulses.

Power Saving Techniques

In one embodiment, a power saving algorithm can be implemented by monitor software and hardware. Implementation of the algorithm may allow the monitoring device to accurately detect a subject's heart and/or pulse rate while reducing the load on the monitor's power supply. Detecting a heart or pulse rate using a power saving algorithm is discussed below with respect to FIGS. 5A-5E.

Figure 5A:
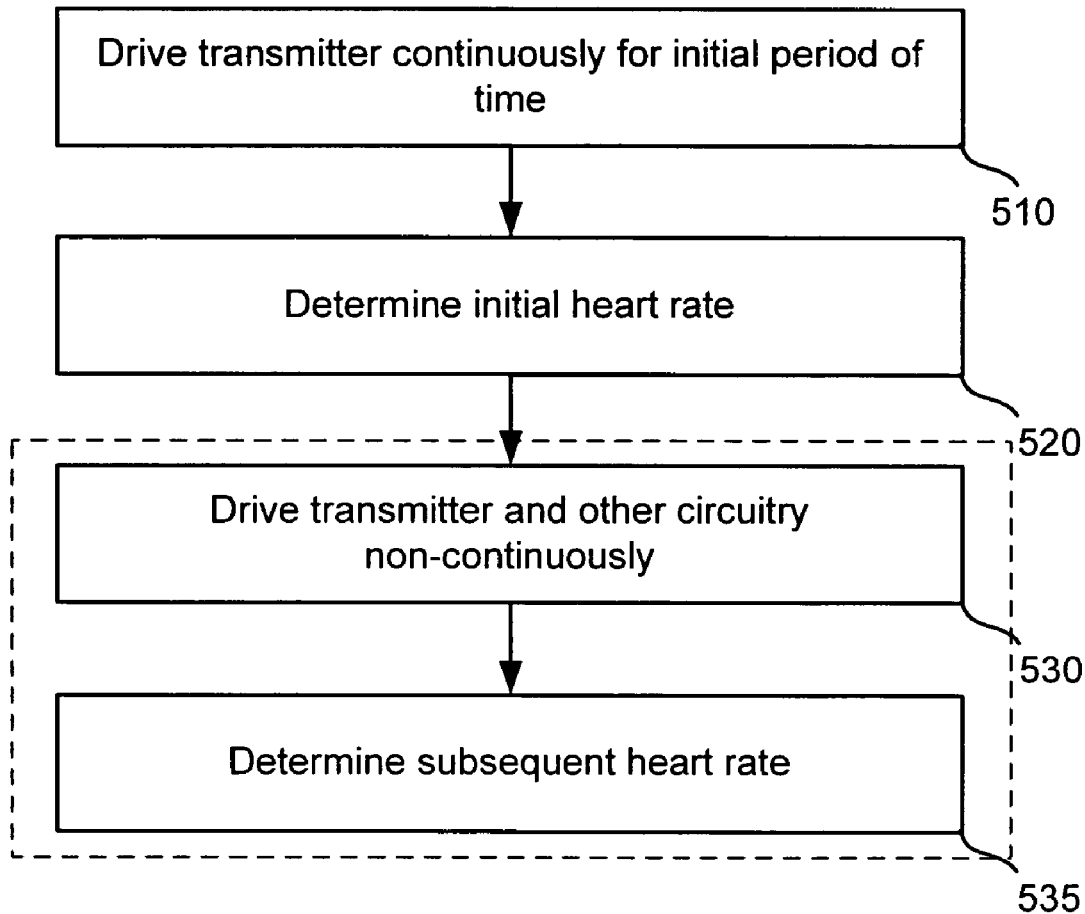
FIG. 5A is a flowchart of an embodiment of a method for saving power while determining a heart rate.

FIG. 5A is a flowchart of an embodiment of a process for determining a heart rate. First, a transmitter element is driven continuously for an initial period of time at step 510. A continuous signal is one that is not intermittent or otherwise provided only a portion of the time. The continuous signal may be an ultrasound signal, infrared signal, radio frequency signal, EKG signal or some other signal directed towards a subject. The signal may be directed at an artery or some other location of a subject being monitored. In one embodiment, the signal transmitted at the subject is directed at an artery of the subject by a wrist worn device or other device in proximity to the subject's skin.

The initial period of time to continuously drive the transmitter may vary. In one embodiment, the initial period of time may be a time period required to detect the heart rate of a subject. In this case, the period of time may not have a set duration. Rather, the period of time can last as long as required to detect the subject's heart rate. In some embodiments, the initial period of time is associated a number of heart beats. In these embodiments, the initial period corresponds to a number of heart beats which are deemed adequate to allow the monitoring device to detect the heart rate of the user. For example, the initial period may last for a time associated with three to five (3-5) beats of the subject's heart. In some embodiments, the initial period of time may last a period of time, such as two to ten (2-10) seconds. In some embodiments, other periods of time, numbers of beats or other criteria may be used to determine the initial period of time.

The initial heart rate of the subject being monitored is determined at step 520. The initial heart rate is derived from the one or more periods between detected beats during the initial period. To determine the initial heart rate, the time between consecutive blood vessel pulses is determined. The heart rate is then determined from the time between the detected pulses. In some embodiments, the initial heart rate is determined as the average period between three or more blood vessel pulses if multiple pulses or beats are detected during the initial period of time. Determining an initial heart rate may be performed as discussed above with respect to FIGS. 4A-4B.

After determining the initial heart rate, the transmitter and other monitor device circuitry are driven non-continuously in step 530. In one embodiment, driving a transmitter and other circuitry non-continuously includes not providing power to the transmitter and some device circuitry and/or components between two or more heart beat pulses. By terminating or reducing the power supply to portions of a monitor between heart beat pulses, the transmitter and other circuitry do not consume power between heart beats. In some embodiments, the transmitter and other circuitry can be shut down for a time period lasting more than one period. In this case, not every consecutive beat will be detected by the system. This is discussed in more detail below with respect to FIGS. 5B and 5C. In any case, the transmitter and other circuitry is powered up just before a particular beat is expected. Once power is provided to the transmitter and/or circuitry circuitry, additional heart beat information can be retrieved and processed.

A subsequent heart rate for the subject is determined at step 535. The subsequent heart rate is the subject's heart rate for a period of time after the initial heart rate is determined at step 520. In one embodiment, the subsequent heart rate is determined from heart rate data collected while the transmitter and other monitor circuits are driven non-continuously at step 530. The subsequent heart rate can be determined from the two most recently detected blood vessel pulses or heart beats, averaged over three or more of the most recently detected pulses or beats, or in some other manner. Steps 530-535 are discussed in more detail below with respect to the flowchart of FIG. 5B, as indicated by the dashed line which surrounds these steps in FIG. 5A.

Figure 5B:
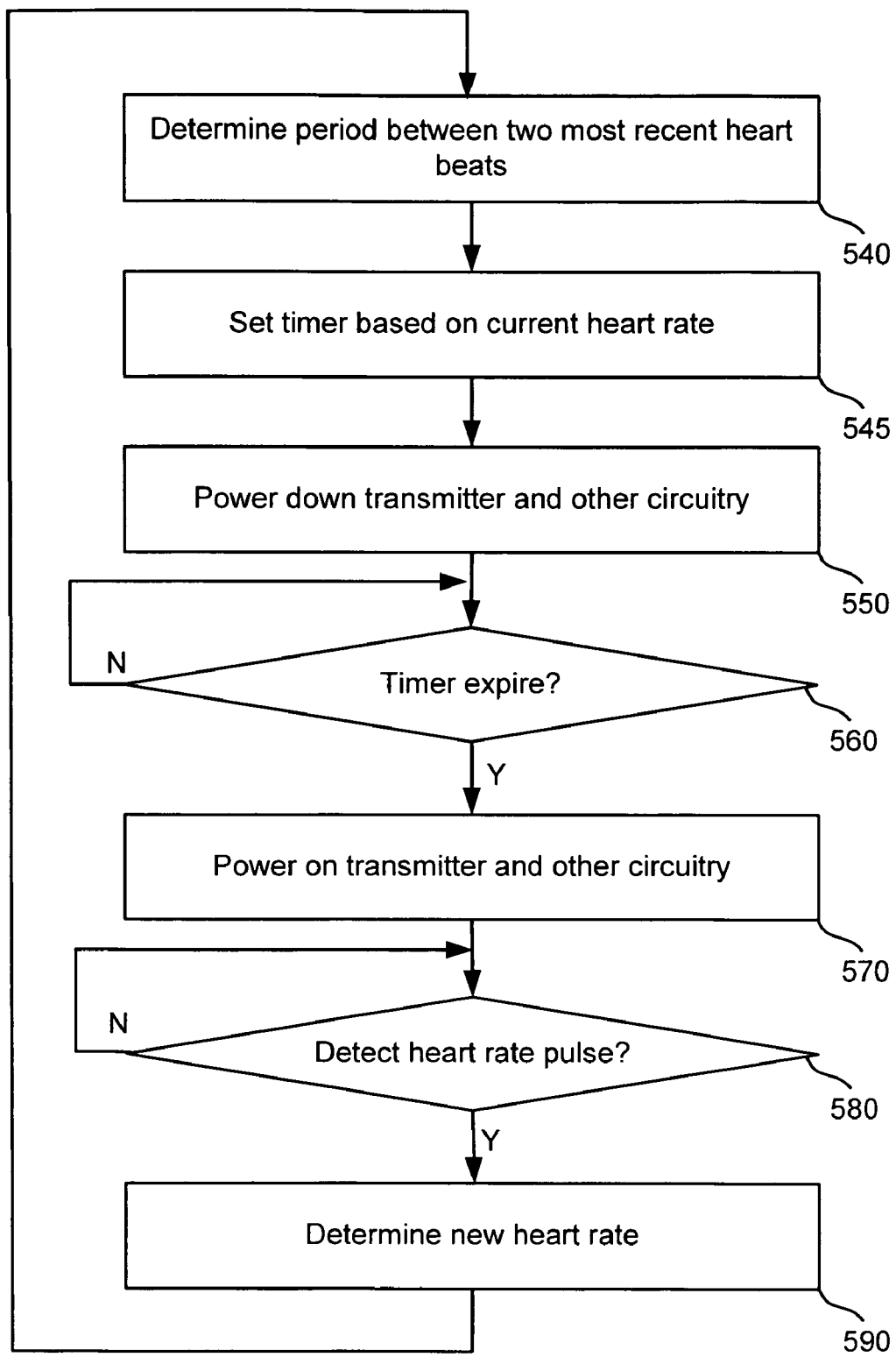
FIG. 5B is a flowchart of an embodiment of a method for driving heart rate detection components and determining a heart rate.

FIG. 5B is a flowchart of an embodiment of a process for driving heart rate detection components and determining a heart rate. In one embodiment, the flowchart of FIG. 5B provides more detail for steps 530-535 of FIG. 5A. First, a period between recently detected heart beats is determined at step 540. As indicated by the arrow from step 590 to step 540, the flowchart of FIG. 5B may repeat several times. During the first cycle of the flowchart, the period between the recent heart beats is associated with data collected during the initial period. This is discussed in more detail below with respect to FIG. 5D. After the initial period has transpired, the time between the recent heart beats may be determined as the time between the two most recently detected heart beats or the average time between three or more heart beats.

After determining the period, a timer is set based on the current heart rate at step 545. For the initial heart rate determined during the initial period, the timer may be set to expire before the period associated with the heart rate is over. Thus, the timer can be set to expire such that the monitor can detect the next occurring heart beat or blood vessel pulse. In some embodiments (e.g., for heart rate data collected after the initial period), the timer can be set to different lengths of time. The different lengths of time may include time periods lasting longer than one heart rate period. The length of time may be set based on several factors. This is discussed in more detail below with respect to FIG. 5C.

In some embodiments, the period of time for which the timer is set may be configured by a user, manufacturer or other entity. In some cases, the timer may be set to expire at approximately 87.5% of the total period detected between the previous heart beats. In this embodiment, the timer will expire with 12.5% of the detected period remaining. The detected period may be the average of two or more periods, an actual period between the previous beats, or some other data. In most cases, this will provide a reasonable amount of time to provide power to previously shut-down monitoring components and detect the next occurring blood vessel pulse or heart beat. Additionally, this one-eighth value can be convenient to implement using digital circuitry. In some embodiments, the timer may be set to expire at some other time before.

After setting the timer, power to the transmitter and optionally other circuitry is shut down at step 550. By not providing power to the transmitter and optionally other signal processing components, the power consumed by the heart rate monitoring device is reduced. The signal processing components may include filters, amplifiers mixers, transducers and other devices and/or components. In some embodiments, a microcontroller may be transitioned into an idle mode at step 550. In this case, the microcontroller may only operate to execute the timer set at step 545 and other important functionality. This reduced power "idle" mode may conserve power consumption by the monitor device.

Though the transmitter and other circuitry may be powered down in step 550, some circuitry and functionality of the heart rate monitor will continue to receive power and function. For example, the display of the heart rate monitor will show the current heart rate, time, and/or optionally other information. Additionally, in some embodiments, a receiving element may still operate. For example, some ultrasonic transducers do not require a power supply in order to "listen" for signals or a beat. In this case, although some circuitry may not be receiving power, a receiving transducer may still detect a subsequent heart beat or pulse. In some embodiments, circuitry associated with receiving a signal from the receiving transducer may be powered on when other circuitry is powered off.

After powering down the transmitter and other circuitry, a determination is made as to whether the timer has expired at step 560. The timer expires once the timer period set at step 545 has transpired. The flowchart remains at step 560 until the timer has expired. Once the timer expires at step 560, power is provided to the transmitter and other circuitry at step 570.

After providing power to the transmitter and other circuitry, a determination is made as to whether a heart rate pulse is detected at step 580. Detecting a heart rate pulse is performed by detecting motion associated with an artery from a reflected signal. As discussed above, the artery motion may be the expansion of an artery as blood flows through the artery, the movement of blood flowing through an artery or other pulse related motion. The reflected signal can be detected by a receiving element in the monitor. This is performed as discussed above with respect to step 420 of the flowchart of FIG. 4A. Once the determination is made that a heart rate pulse is detected, the new heart rate is determined at step 590. In one embodiment, the period between the previous pulse detected and the pulse detected at step 580 is determined. The new heart rate is determined by taking the inverse of the period between these two pulses. In some embodiments, the period between the most recent pulses is averaged with the prior pulse periods in order to determine the heart rate. Once the new heart rate is determined, the flowchart of FIG. 5B returns to step 540.

Figure 5C:
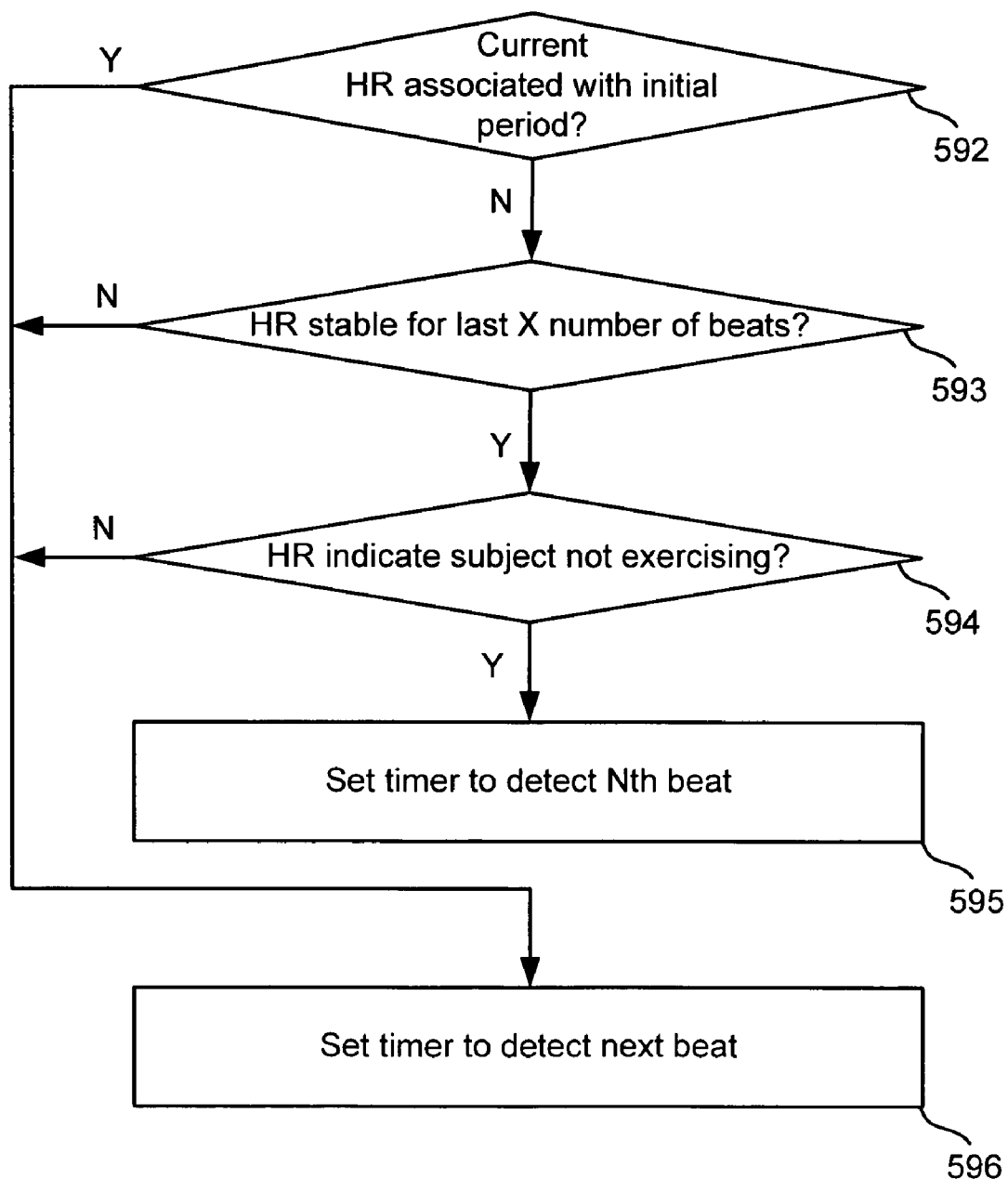
FIG. 5C is a flowchart of an embodiment of a method for setting a timer to detect a heart pulse.

As discussed above, setting a timer during which to power down monitor components can be done based on several factors. FIG. 5C is a flowchart of an embodiment of a process for setting a timer to detect a heart rate pulse. In one embodiment, the flowchart of FIG. 5C provides more detail for step 545 of FIG. 5B. First, a determination is made as to whether the currently detected heart rate is associated with the initial period at step 592. In this case, a determination is made as to whether the current heart rate was determined from data collected during the initial period. If the current heart rate is associated with the initial period at step 592, the flowchart of FIG. 5C continues to step 596. At step 596, the timer is set to detect the next occurring beat. In this case, the timer is set to expire in a length of time less than the period associated with the currently detected heart rate. Thus, the timer is set to expire to allow the monitor to detect the next occurring heart beat. If the current heart rate is not associated with the initial period, the flowchart of FIG. 5C continues to step 593.

If the current heart rate is not associated with the initial period, a determination is made as to whether the heart rate has been stable for the last x number of beats at step 593. In this case, "x" is a number, such as an integer. Thus, a determination is made as to whether the period between the last x number of beats is the same. In one embodiment, the period between the last x number of beats may not necessarily be the same, but within a particular margin, for example, a margin of plus or minus five percent. The number of beats x may depend on the user, the user's condition or other information. For example, if the user has a heart condition, it is undesirable to let a large number of beats occur without determining if the user's heart rate is increasing or decreasing. In some embodiments, the number of beats x associated with step 593 may be three to five (3-5) beats. If the heart rate is determined to be stable for the last x number of beats at step 593, the flowchart of FIG. 5C continues to step 594. If the heart rate is determined to be unstable for the last x number of beats, the flowchart of FIG. 5C continues to step 596. In this case, since the heart rate is not stable, it is possible that the user's heart rate is either increasing or decreasing. In either case, it is desirable to detect the next occurring beat or pulse in order to provide accurate information, rather than waiting to detect a later heart beat.

If the subject's heart rate has been determined to be stable at step 593, a determination is made as to whether the detected heart rate indicates the monitored subject is not exercising at step 594. In one embodiment, a heart rate within a certain range may indicate a subject is or is not exercising. Heart rate ranges associated with strenuous activity are well established for different ages of subjects. Thus, if a subject's heart rate is within a particular range associated with strenuous activity, it can be assumed that the subject is exercising or performing some type of strenuous activity. In one embodiment, a heart rate range associated with non-strenuous activity may be between 40%-55% of the user's actual or estimated maximum heart rate. Other heart rate ranges may also be used based on additional factors, such as age and fitness of the subject. If the user's heart rate indicates that the user is not currently exercising, the flowchart of FIG. 5C continues to step 595. If the user's heart rate indicates the subject is exercising engaged in strenuous activity, or otherwise has a heart rate above a normal resting heart rate, the flowchart of FIG. 5C continues to step 596.

A timer is set to detect an Nth heart beat at step 595. In this case, a number of beats may be skipped in determining the heart rate of the user. Beats may be skipped because the user has had a stable heart rate for the last x number of beats and is not determined to be exercising or exerting himself. As such, the user's heart rate is likely not to change within the next few heart beats. In one embodiment, the number of beats to set the timer to skip may be based on user information (including user age, user fitness level, user health condition, etc.), the use of the heart rate monitor device, the desired accuracy of the monitor, and other information. In one embodiment, two to five (2-5) heart beats or pulses may be skipped such that the timer may detect the third, fourth or fifth heart beat for the user.

FIG. 5D illustrates an example of a heart rate monitor power signal over time. FIG. 5D includes a heart pulse or heart rate signal, a heart rate monitor power signal below the heart pulse signal, and a timeline under the monitor power signal. The heart pulse signal includes six heart pulses, represented by spikes in the signal. For each pulse in the signal, a pulse of flowing blood is generated through an artery of the subject. The timeline represents time transpiring from left to right.

The heart rate monitor power signal transitions between a power on state and power off state over the course of the power signal. When the monitor is in the power on state, the monitor is providing full power to the monitor transmitter, signal processing components and other circuitry. When the monitor is in the power off state, selected portions of the monitor may still be receiving some power (such as the monitor display, microcontroller, etc.), but the monitor transmitter and signal processing components may not be receiving power.

The timeline of FIG. 5D illustrates an initial period of time $t_i$. During the initial period of time $t_i$, four pulses occur in the heart pulse signal and the monitor power signal is maintained at the power on state. The number of heart beat pulses may vary during which an initial period may last. After the initial period ends, the monitor determines the heart rate period $T_i$ associated with the heart rate signal during the initial period $t_i$ and sets the monitor power signal to the power off state. The monitor power signal transitions back to the power on state at a time just before the determined period $T_i$ expires from the last detected pulse. In the example illustrated, the monitor power signal transitions back to the power on state at a time $T_i-(0.125*T_i)$ after the fourth pulse. The time during which the heart rate power signal may power down between pulses may vary. The actual period between the fourth pulse and the fifth pulse is illustrated as $T_s$.

In some embodiments, a beat processing mechanism or process may result in a delay in terminating power to some monitor components after the most recently detected beat. For example, a mechanism may implement a time delay after detecting a heart beat, such that the monitor is not powered down until the time delay expires. The time delay may allow the monitor to process a detected heart signal, confirm that the detected signal is actually a heart beat, or perform other processing. The length of the time delay may depend on the particular monitor being implemented as well as the beat or pulse detected. For example, the time delay may lie within a time range of fifty milliseconds to four hundred milliseconds. In other embodiments, the time delay may be derived from the heart rate period, for example 0.02 times the heart rate period to 0.4 times the heart rate period. Other ranges and/or values, including a time delay of zero, may be used as a time delay as well.

An example of a time delay $T_p$ is illustrated in FIG. 5D. In particular, the time period $T_p$ is a time period during which the monitor is set to a power-on level after the last heart beat occurs in the initial period, before power is terminated to portions of the monitor. In this case, the monitor may determine the validity of a detected heart beat or perform other processing during the time Tp. As discussed above, the time delay may vary according to the sharpness and clarity of the heart signal detected. As illustrated in FIG. 5D, the delay period $T_p$ can be subtracted from $T_s$ and/or $T_i$ for calculating the period during which power is terminated to monitor components. That is, the time during which power is terminated will be $(T_s-0.125*T_s-T_p)$ and $(Ti-0.125*Ti-T_p)$, respectively.

When the monitor power signal transitions back to a power on state, the monitor transmits a signal towards a subject during a window of time. The window of time is associated with an expected heart beat. For example, in FIG. 5D, the monitor may transmit a signal towards a subject for a window of time associated with the time that the heart rate monitor power signal is at the power on state around fifth pulse illustrated in the heart pulse signal (the first pulse after the initial period). Thus, the window of time begins before a pulse is expected to occur and ends sometime after the pulse is expected to occur.

After detecting the fifth pulse, the monitor power signal transitions to a power down state again. The power signal then transitions to a power on state at a time $T_s-(0.125*T_s)$ after the fifth pulse in order to detect the sixth pulse. After detecting the sixth pulse, the monitor detects the heart rate period between fifth and sixth pulse, and sets the monitor power signal to the power down state. In this manner, the monitor may continue to enter the power down state between expected pulses, and transition to a power on state at a time based on the heart rate period associated with previous pulses.

In some embodiments, the monitor power signal may transition to a power off state for a period of time derived from more than period. For example, after powering down in response to detecting a pulse that occurs after the initial period, the monitor power signal can transition to a power on state at a time $T_s-(0.125*T_{avg})$, wherein $T_{avg}$ is the average period between three or more previous detected pulses. Thus, rather than transitioning to a power on state just before a period of time associated with the previous two pulses period, the power on state is transitioned to based on an average of two or more detected pulse periods. In some cases, transitioning to a power on state based on an average value for two or more periods may reduce the influence, or error, due to any false signals which were incorrectly determined to be a pulse.

As discussed above with respect to FIG. 5C, a timer may be set such that one or more beats are not detected (e.g., one or more beats are skipped) by the heart rate monitor. In this case, the time period associated with a heart rate monitor power off state may last for multiple heart rate periods T. FIG. 5E illustrates an example of a heart rate power signal, wherein the signal is powered down for multiple heart rate periods T. FIG. 5E includes a heart rate signal, a heart rate monitor power signal and a timeline, similar to FIG. 5D. Within the initial period of time $t_i$ illustrated in the timeline of FIG. 5E, three heart beats occur in the heart beat signal and the heart rate monitor power signal is at the power on state. The number of heart beat pulses may vary during which an initial period may last. After the initial period of time $t_i$, the monitor determines the average period associated with the heart rate pulses during the initial period. The heart rate monitor power signal then transitions from a power on state to a power off state. The monitor power signal transitions to a power on state at some point before the fourth heart beat. The fourth heart beat occurs at a time $T_s$ after the third heart beat. After the fourth heart beat is detected, the monitor determines the heart rate period $T_s$ between the fourth heart beat and the third heart beat, and transitions to a power down state.

Upon powering down after the fourth heart beat, the monitor remains in the power off state for a period of time lasting just less than twice the period of the previously detected heart rate period $T_s$. In the particular example illustrated, the heart rate monitor power signal transitions to a power off state until a time period equal to $2T_s-(0.125*T_s)$ has transpired since the fourth heart beat. In this case, the monitor remains in the power down state until while the fifth heart beat in the heart beat signal occurs. The monitor power signal then transitions to a power on state to detect the sixth heart beat, as illustrated in FIG. 5E.

Different embodiments of a monitor are discussed below. The embodiments discussed include implementation of a monitor on a circuit board, using a gel pad, using an adhesive member, and other embodiments. The embodiments will be discussed with reference to an ultrasonic monitor. The references below to an ultrasonic monitor are for purposes of discussion only, and are not meant to limit the scope of the monitor herein to this type of technology. In particular, the embodiments of the monitor discussed below are intended to be suitable for use with laser, radio frequency and other technologies suitable for use with a heart rate monitor.

Heart Rate Monitor on a Circuit Board

One embodiment of an ultrasonic monitor system is implemented on a printed circuit board (PCB). PCB technologies such as surface mount (SMT) and chip-on-board (COB) can be used to implement the monitor on a PCB. Implementing the circuitry on a PCB integrates the monitor system to a very small footprint. This allows for a more efficient system, lower power requirement, consistent product performance and reduced production cost.

Implementing the monitor system on a PCB allows for easy construction of an aperture, or air gap, portion. To generate the air gap portion, one or more sections of the outer layer of the PCB are removed. The transducers are then placed over the air gap portion. This creates an air gap portion having one or more air gaps underneath the transducer elements. The air gap portion reflects ultrasonic signals away from the PCB and towards the desired direction. The air gap is more effective and much more easily constructed than foam layers of prior systems. Additionally, the transducer elements are mechanically isolated as a result of the air gap, thereby reducing any dampening or loading effect on the transducers from contact by any other material. The air gap also serves to significantly reduce if not eliminate crosstalk noise between the transducers. In some embodiments, additional layers may be removed from the PCB to generate an air gap portion with a larger thickness. In this case, additional etching, drilling or other methods may be used to control the depth of the air gap. In some embodiments, an air gap may be generated that penetrates the entire circuit board. This method provides for simple generation of an air gap that effectively reflects the ultrasound signal.

The ultrasonic monitor transmits ultrasound signals more efficiently than prior monitors. The ultrasonic monitor transducers are mounted directly to the PCB using conductive epoxy or solder paste. Transducers of previous systems are typically glued entirely to a supporting structure, such as a glass base plate. Attaching the entire surface of the transducers to a supporting structure creates a mechanical load that dampens the vibration of the transducers. The dampening reduces the efficiency and draws power from the ultrasonic signal. With a minimized load, transducers of the present invention can generate the same ultrasound signals of previous systems using less power.

The PCB may include several layers, for example, a power layer, a ground layer and an insulating layer. The insulating layer can isolate the transducers from the monitor system circuitry. In some four layer PCBs, there are four copper layers and three insulating layers. Two copper layers are outer layers and two are inner layers. In one embodiment, to isolate the two transducers electrically so that they won't interfere with the rest of the circuitry on the PCB, one of the inner copper layers immediate next to the transducers can be used as a ground plane or ground layer. This inner copper layer ground plane will shield RF interferences generated or received by the transducers. This prevents the circuitry from causing interference with the transducer signal transmissions. In one embodiment, one surface of the PCB may be used to implement the monitor system circuitry and the opposite surface may be used to mount the transducers. In another embodiment, the transducers may not be implemented on the same PCB as the monitor system circuitry.

Figure 6:
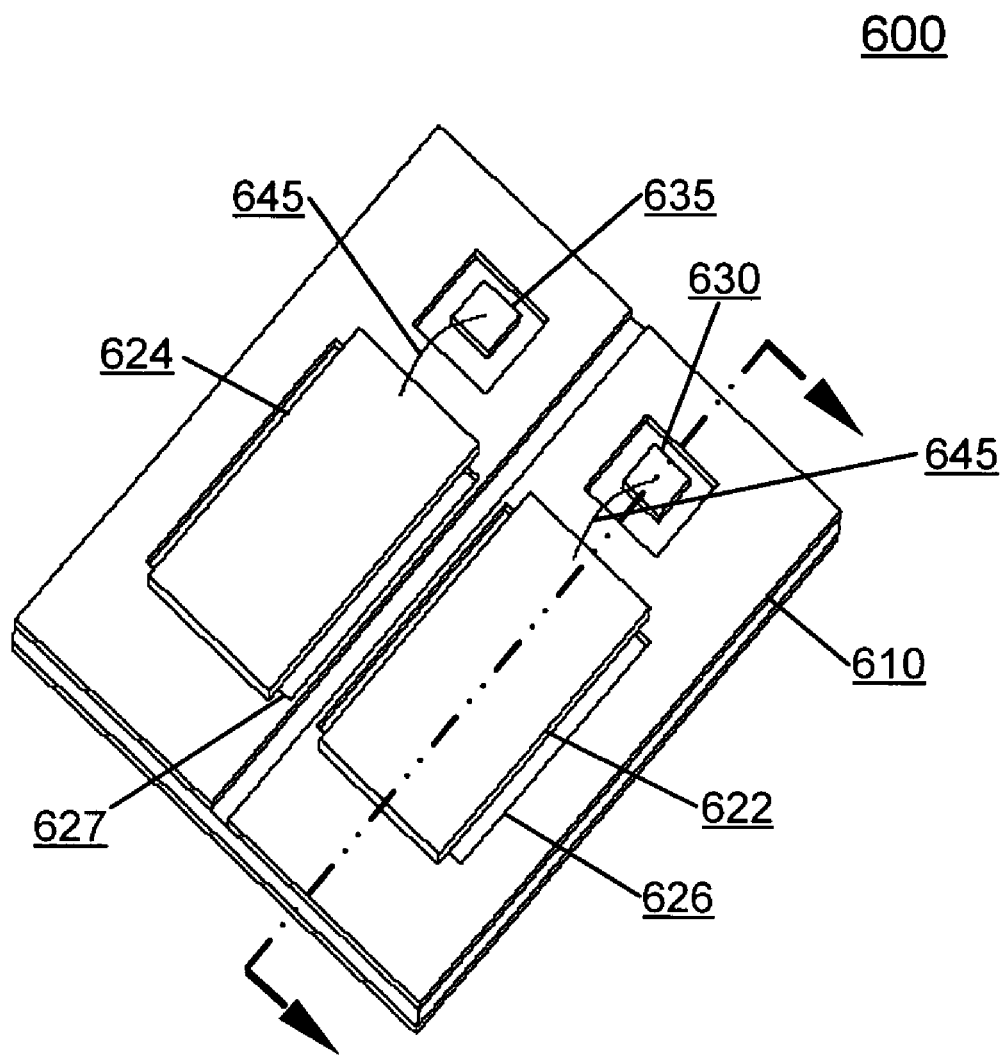
FIG. 6 illustrates one embodiment of a perspective view of an ultrasonic monitor on a PCB having an air gap.

FIG. 6 illustrates a top view of one embodiment of a monitor 600 implemented on a PCB. Monitor 600 includes outer layer 610, a first transducer 622 and a second transducer 624 mounted to outer layer 610, air gaps 626 and 627 residing underneath the transducers 622 and 624, respectively, dedicated copper pads 630 and 635, and connecting wires 640 and 645 connected between the dedicated copper pads 630 and 635 and the transducer elements 622 and 624, respectively. In one embodiment, the outer layer 610 is composed of a conducting material such as copper plated in tin or gold.

Figure 7:
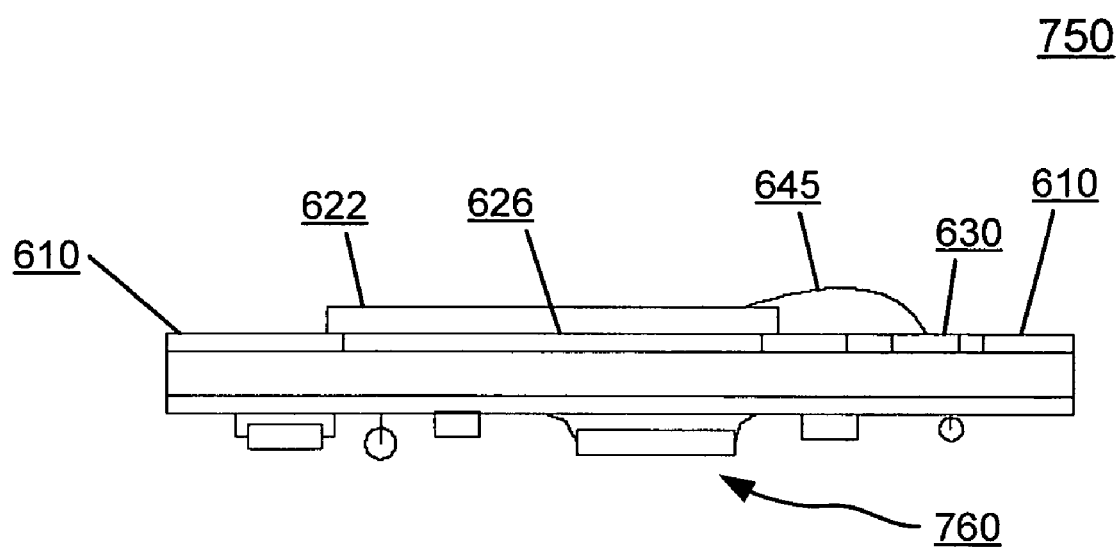
FIG. 7 illustrates one embodiment of a side view of an ultrasonic monitor on a PCB having an air gap.

FIG. 7 illustrates a side view of the monitor 750 implemented on a PCB and further illustrates circuitry 760 attached to the opposite surface of the PCB. Circuitry 760 includes surface mount ICs and electrical components such as resistors and capacitors that can implement the electrical system of the ultrasonic monitor.

Most, if not all, of the construction of the PCB can be automated. Application of solder paste, placement of the transducer elements and wire bonding can all be automated by existing PCBA production technologies. This reduces manufacturing cost significantly. For typical electronic components such as resistors, capacitors, and integrated circuits in surface mount packages, a stencil is used to apply solder paste to the PCB on one side first. An automatic pick and place machine then places these components. The PCB is then subjected to an infrared (IR) furnace which melts solder paste and forms electrical connections between the components and the underlying circuit pre-etched on the PCB. The same steps can be applied to mount the transducer elements on the opposite side of the PCB. This tremendously reduces the production cost and enhances product performance consistency.

Air gap portions 626 and 627 of FIGS. 6 and 7 are constructed by removing a portion of the outer layer. Chemical etching can be performed to remove a portion of the outer layer of a PCB. Accordingly, the depth of the air gap portion is the thickness of the layer removed. The area of outer layer 610 etched away is proportional to the surface area of the transducers 622 and 624. Air gap portions 626 and 627 are constructed so that the transducer elements 622 and 624 slightly overlap the air gap portion. This overlap of the transducer allows the ends of the transducers to be mounted to the outer layer of the PCB.

Figure 8A:
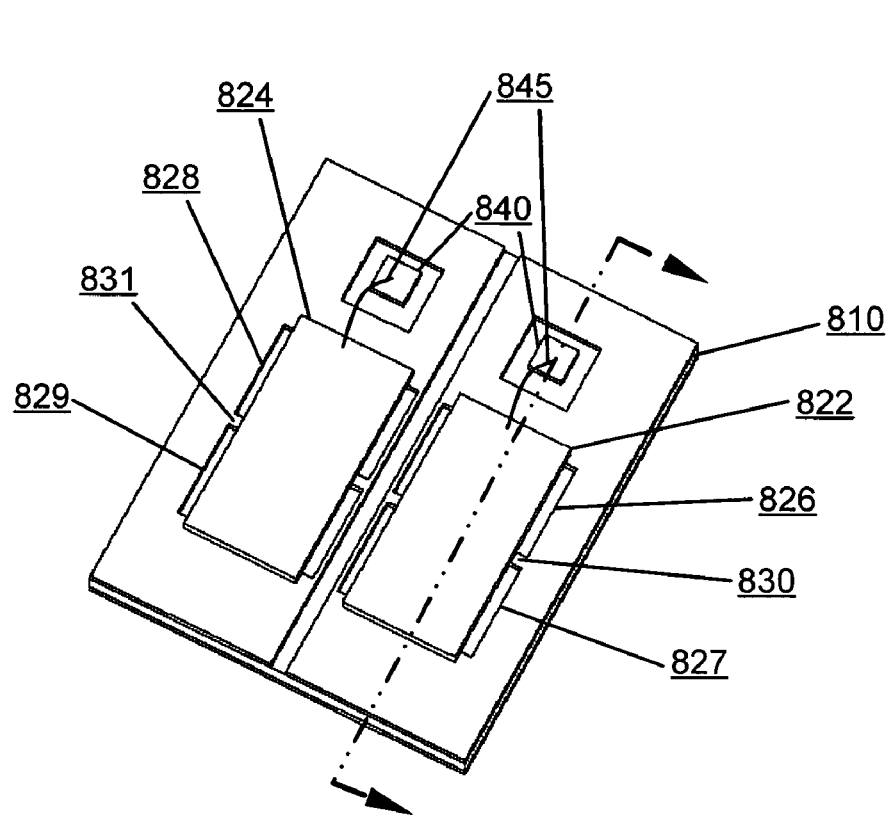
FIG. 8A illustrates one embodiment of a perspective view of an ultrasonic monitor on a PCB having an air gap with a supporting member.
Figure 8B:
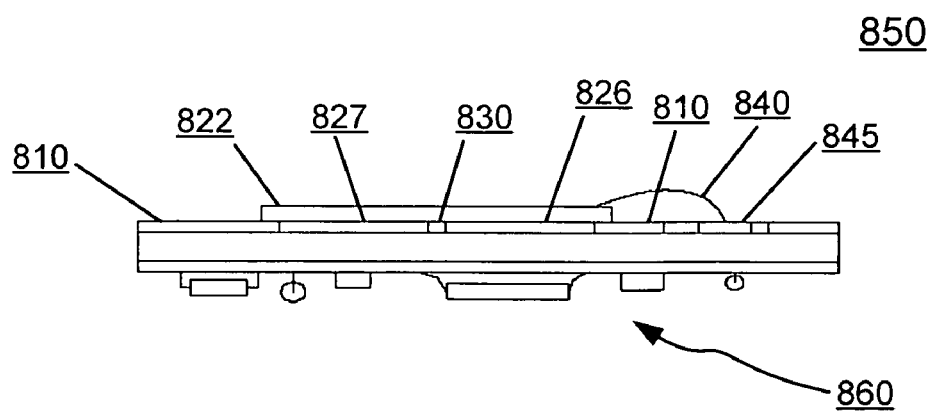
FIG. 8B illustrates one embodiment of a side view of an ultrasonic monitor on a PCB having an air gap with a supporting member.

The air gap portion of the present invention may be implemented in several ways. In the embodiment illustrated in FIGS. 6 and 7, the air gap portion is a single undivided area underneath each transducer. The air gap extends about as long as the width of the transducer and slightly shorter than the length of the transducer. FIG. 8A is a top view of an embodiment of a monitor 800 implemented on a PCB. Monitor 800 includes PCB outer layer 810, transducers 822 and 824 connected to the outer layer, air gaps 826 and 827 underneath transducer 822 and separated by supporting member 830, air gaps 828 and 829 underneath transducer 824 and separated by supporting member 831, copper contact pads 840, and connecting wires 845 connecting copper pads 840 to transducers 822 and 824. FIG. 8B is a side view of monitor 800 implemented on a PCB and further illustrates circuitry 860 attached to the opposite surface of the PCB. The air gap portion of FIGS. 8A and 8B includes two air gaps. The air gap portion extends about as long as the width of the transducer and slightly shorter than the length of the transducer. However, the air gap portion for each transducer includes a support member. Thus, the air gap portion for transducer 822 is comprised of air gap 826, air gap 827 and support member 830 and the air gap portion for transducer 824 is comprised of air gap 828, air gap 829 and support member 831.

The support member is constructed by leaving a portion of the outer layer of the PCB over which the transducer will reside. In the embodiment of FIGS. 8A and 8B, support members 830 and 831 are thin strips extending across the width of the air gap portion and located at about the middle of the length of the transducer. In different embodiments, the support members can be implemented with different shapes and locations within the air gap portion of the PCB. For example, the support member can be implemented as a strip extending less than the entire width of the air gap portion, a strip along the length of the air gap portion, or as a plurality of small regions within the air gap portion. When implemented as one or more regions, the supporting member can be isolated from the remainder of the outer layer or contact with a portion of the outer layer. The support member can support a transducer should the transducers receive pressure from an outside force.

Figure 9A:
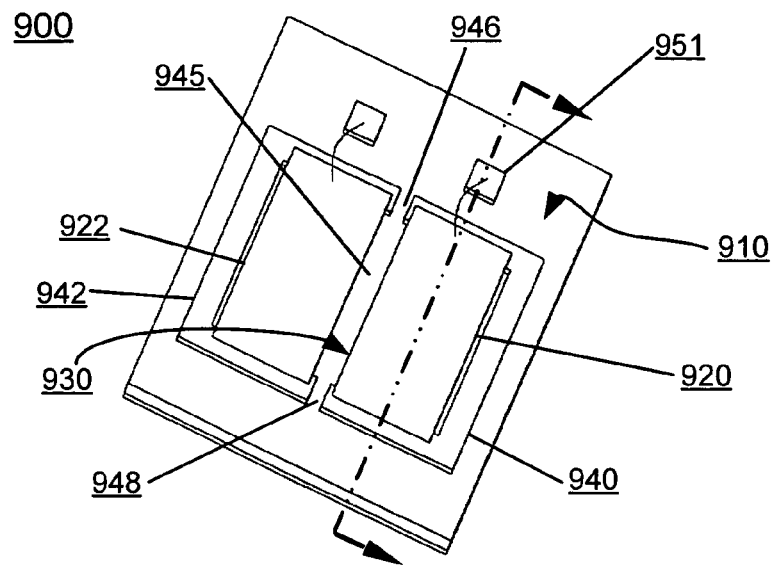
FIG. 9A illustrates one embodiment of a perspective view of an ultrasonic monitor on a PCB having one air gap shared by two transducers.
Figure 9B:
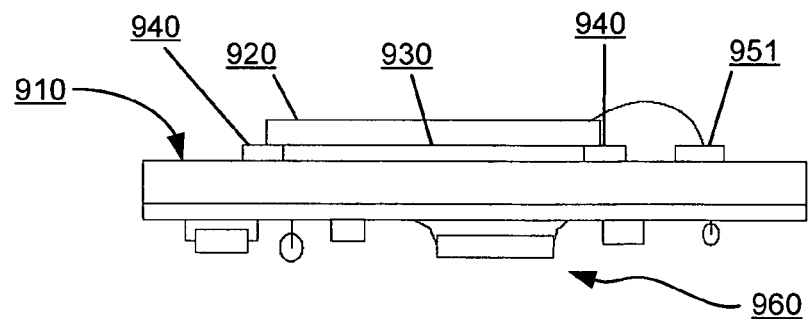
FIG. 9B illustrates one embodiment of a side view of an ultrasonic monitor on a PCB having one air gap shared by two transducers.
Figure 9C:
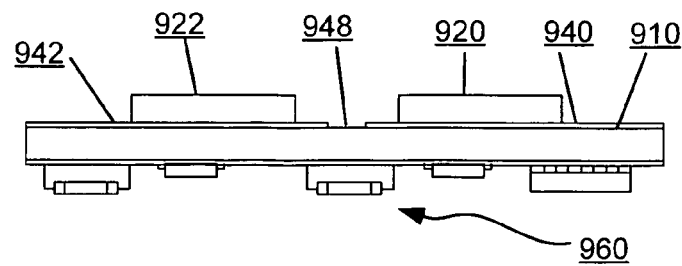
FIG. 9C illustrates one embodiment of a front view of an ultrasonic monitor on a PCB having one air gap shared by two transducers.
Figure 10A:
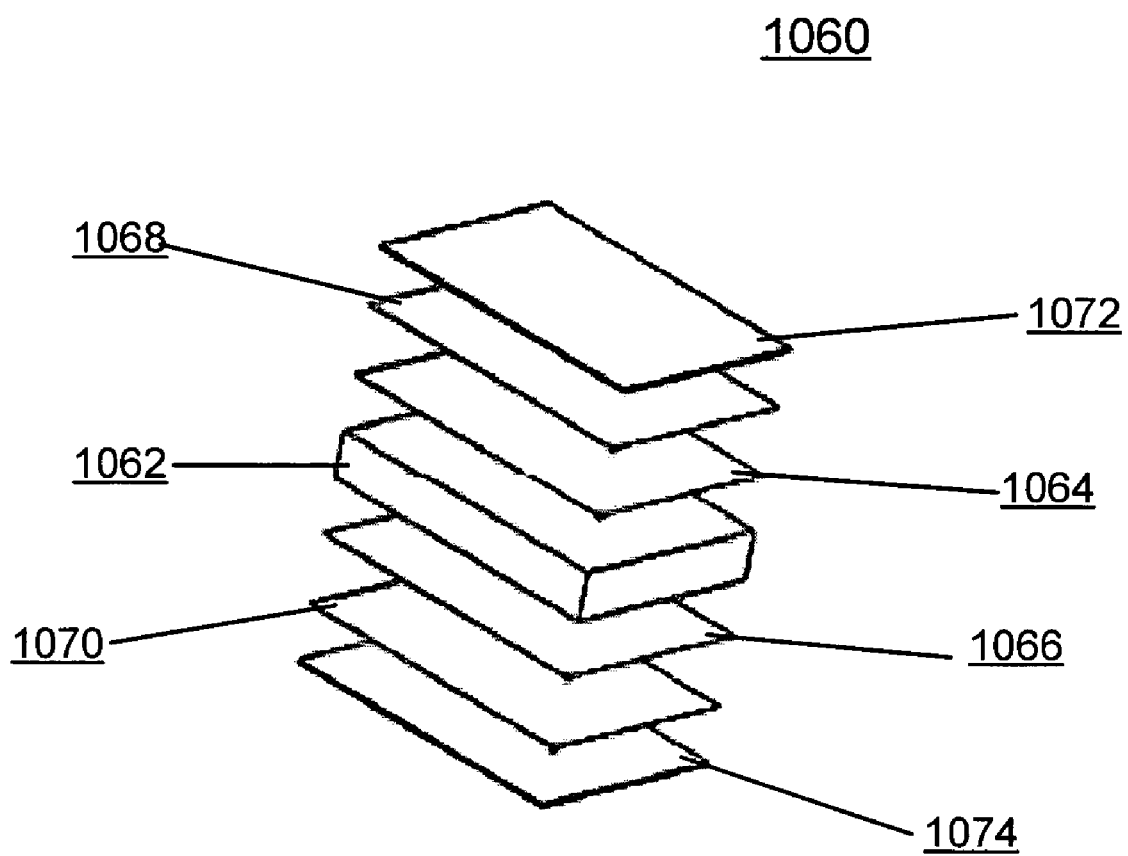
FIG. 10A illustrates one embodiment of a gel pad.
Figure 10B:
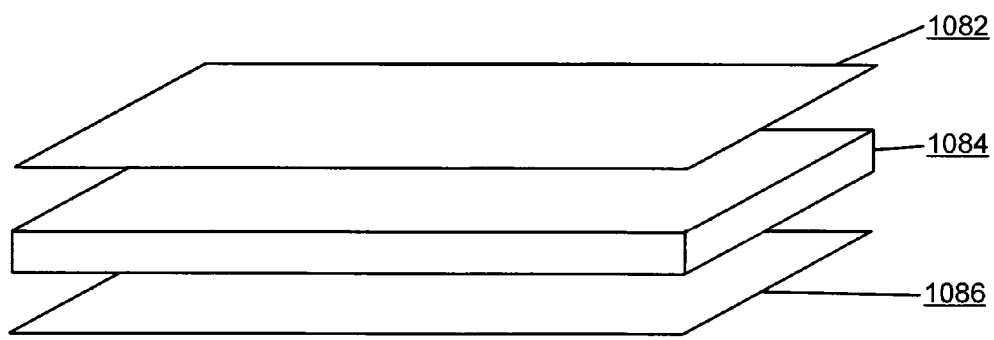
FIG. 10B illustrates a perspective view of an adhesive member.
Figure 10C:
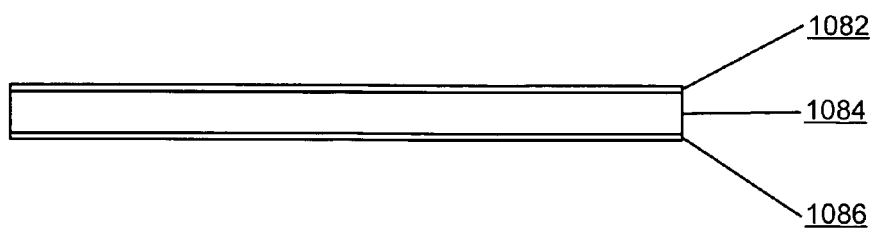
FIG. 10C illustrates a side view of an adhesive member.

FIGS. 9A-C depict an embodiment of a monitor 900 implemented on a PCB. FIG. 9A provides a top view of monitor 900. Monitor 900 includes first layer 910, mounting layer 940 and 942 attached to the first layer, transducers 920 and 922 mounted to mounting layers 940 and 942, respectively, air gap 945 located underneath transducers 920 and 922, air gap channels 946 and 948 located between mounting layers 940 and 942, and copper pad 951. Mounting layers 940 and 942 have a u-shape. The mounting layers can be implemented by removing a portion of a PCB layer to form the u-shaped layer or by attaching a u-shaped member to a layer of the PCB. In some embodiments, one or more mounting layers having positions and shapes that differ from those illustrated in FIGS. 9A-C can be implemented to support and provide an air gap underneath each transducer. FIG. 9B is a cut-away side view of monitor 900 from the perspective indicated by the arrow in FIG. 9A. FIG. 9B illustrates the monitor implemented on a PCB with transducer 920 mounted to mounting layer 940, mounting layer 940 attached to first layer 910, air gap 930 underneath transducer 920, and circuitry 960 attached to the opposite surface of the PCB. FIG. 9C is a front view illustrating the monitor 900. In the monitor of FIGS. 9A, 9B and 9C, the outer layer is removed to form an undivided air gap underneath transducers 920 and 922. The removed portion extends around the transducers to reveal portions of the underlying layer 910 not covered by the transducer elements.

As illustrated in the PCB of FIGS. 7A-B, 8A-B, and 9A-C, the transducer is mounted to the outer layer of the PCB where the transducer length slightly overlaps the air gap portion. In some embodiments, the air gap portion can be formed such that the transducer is mounted to the PCB where the transducer width slightly overlaps the air gap. In one embodiment, the width and length of the air gap portion will not be made larger than the width and length of the transducer elements. This prevents any silicone based epoxy or molten thermoplastic gel that may be applied to the transducer from getting into the air gap portion. If epoxy or gel does penetrate the air gap, the acoustic impedance of the gel and the exposed fiber glass material comprising the PCB are different enough that the ultrasound energy will still be effectively reflected towards the desired direction. Since the air gap is relatively thin, the loss of energy, if any, will be negligible.

Oil-Based Transmission Media for Ultrasonic Frequency Transmission

In one embodiment, a transmission medium may be implemented as an oil based transmission medium. An oil-based transmission medium may be biocompatible, and used to transmit an ultrasonic frequency signal between an ultrasonic monitor and a subject. The biocompatible oil-based transmission medium may be in contact with an adhesive member, a subject, ultrasonic monitor transducers, or a protective material. The protective material may have a surface that is directly or indirectly in contact with the transducers, such as a room temperature vulcanizing (RTV) silicone rubber layer adhesive. A protective material such as an RTV layer can be a molded material that encompasses the transducers and a portion of the PCB outer surface and is mounted to the PCB. Protective material layers in an ultrasonic monitor are discussed in more detail below. Oil-based transmission mediums are generally transparent to ultrasound. Thus, the energy loss during transmission is minimized significantly. This allows the ultrasonic monitor to effectively measure both the blood flow rate and cardiac output accurately. In some embodiments, the oil-based transmission medium may be applied directly to the ultrasonic monitor and/or the user's skin.

Biocompatible oil-based transmission mediums consist primarily of a wax component and an oil component. The amounts of these components may determine whether the biocompatible oil-based transmission medium has a balm-like or lotion-like composition. Both balm and lotion-like transmission mediums may transmit ultrasonic frequency signals, but the different consistencies may be better suited for different uses. Both balm-like and lotion-like oil based transmission mediums are easy to apply, easy to clean and may be reapplied as often as required. A balm-like oil-based transmission medium may be used as encapsulating moldings over a portion of the ultrasonic monitor. This is discussed below.

In one embodiment, a wax component of an oil-based transmission medium may be comprised of a natural low melting wax. Examples of natural low melting waxes include beeswax, carnauba wax, and candelilla wax, etc Beeswax has a melting point of about 62°-65° C., carnauba wax has a melting point from 82°-83° C., and candelilla wax has a melting point from 68°-73° C. In one embodiment, any low melting wax may be used which has a melting point between 37°-90° C. In some embodiments, FDA approved fully-refined paraffin waxes and microcrystalline waxes having a melting point within this given range can also be used as a total or partial substitute of a wax component.

The oil component of an oil-based transmission medium may be a natural oil, such as a plant based oil. Plant based oils are extracted or squeezed from their corresponding plants, flowers or fruits, or may be a mixture of several fatty acid esters. This process is well known in the art. Examples of suitable natural oils for an oil-based transmission medium include almond oil, aloe vera oil, apricot kernel oil, avocado oil, calendula oil, evening primrose oil, grape seed oil, hazelnut oil, jojoba oil, macadamia oil, olive oil, pumpkin seed oil, rose hip oil, safflower oil, sesame oil, sunflower oil, walnut oil, wheat germ oil, canola oil, coconut oil, tea tree oil, and vitamin E oil. In some embodiments, natural oils suitable for use in an oil-based transmission medium need not be liquids at room temperature, but may have a butter-like consistency instead. Examples of butter-consistency natural oils include coconut butter, cocoa butter, jojoba butter, shea butter, most hydrogenated oils and lanolin. In some embodiments, some highly refined petroleum based oils, such as mineral oil and petrolatum, can be used as partial substitutes for plant based oils.

In addition to the wax and oil components, some amount of an "essential oil" can be added to the oil-based transmission medium. In one embodiment, an essential oil is an oil or other extract from a plant that is scented, aromatic, acts as a moisturizer, or repairs skin damage. Examples of essential oils may include bay leaf, bergamot, caraway, cardiman, cedar, citronella, eucalyptus, frankincense, gardenia, juniper, orange, patchouli, rosemary, and tea tree oil. Essential oils may be used to add fragrance, provide healing effects, moisturize, change the oil consistency or provide some other feature to the biocompatible oil based transmission medium.

An oil-based transmission medium may also include some amount of water. Most natural waxes due to their acidity can be partially soluble in water. The water may be used to soften the transmission medium composition and provide a jelly or cream-like consistency. The addition of a water component in an oil-based transmission medium will not affect the biocompatibility of the transmission medium. An oil-based transmission medium having a jelly or cream-like consistency is well suited to be applied to the subject and/or the ultrasonic monitor from a lotion or cream applicator.

Figure 11A:
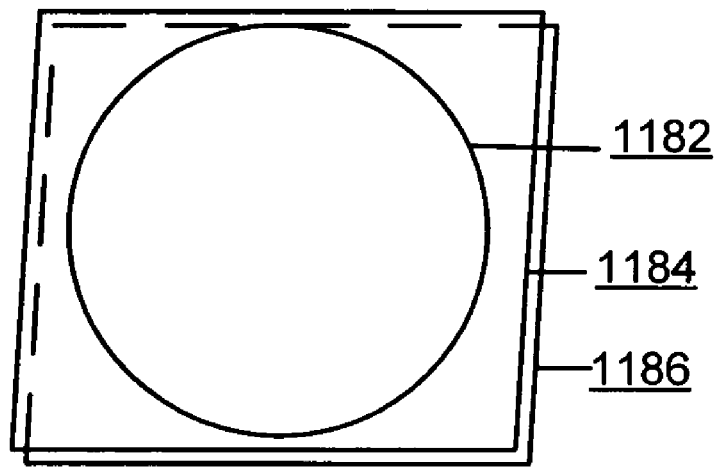
FIG. 11A illustrates one embodiment of a perspective view of a oil-based transmission medium component.
Figure 11B:
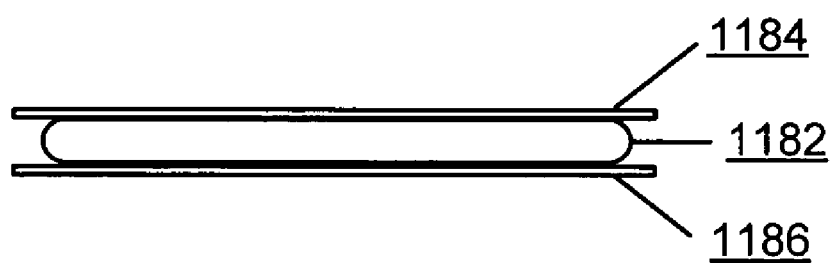
FIG. 11B illustrates one embodiment of a side view of a oil-based transmission medium component.

The ratio of wax and liquid (liquids such as oil and water) in an oil-based gel that is biocompatible with a user's skin can vary. In one embodiment, a wax to liquid ratio of about 1:1 to 1:3 produces a material having a soft, solid-like consistency that maintains a fixed shape. In one embodiment, the fixed shape may be a disc, a rod or some other shape that can be positioned between an ultrasonic monitor and the user's skin. An example of a disc shaped transmission medium is illustrated in FIGS. 11A and 11B and discussed in more detail below. A transmission medium of this type, having a soft but solid-like consistency, may be pliable upon rubbing onto the skin and feel dry with these compositions. A fixed shape oil-based transmission medium may be used as encapsulating moldings over a portion of the ultrasonic monitor. This is discussed in more detail below.

An oil-based transmission medium having a wax to liquid ratio of about 1:4 has the consistency of a jelly, similar to a Vaseline or petrolatum material. If the ratio is increased to between 1:6 and 1:10, the oil based transmission medium may have a consistency of a cream or lotion. Regardless of the consistency of the oil based transmission medium, it may act as an effective ultrasound transmission medium between the ultrasonic monitor and the skin of a user. In one embodiment, the oil based transmission medium to be used with an ultrasonic monitor may be between 1:1.5 to 1:4, such that the transmission medium composition has a dry feel and is not too messy to apply. An oil-based transmission medium having a cream or lotion-like consistency is well suited to be applied to the subject and/or the ultrasonic monitor from a lotion or cream applicator.

As discussed above, the ratio of wax to liquid in the oil based transmission medium may determine whether the consistency of the transmission medium is lotion-like or balm-like. For a lotion-like transmission medium, the transmission medium may be characterized by its viscosity property. The viscosity may be determined by the standard ASTM D2196. This standard determines the viscosity of coatings and related materials by measuring the torque on a spindle rotating at a constant speed within the material. In one embodiment, a Brookfield RVF viscometer may be used to determine the viscosity characteristic using the ASTM D2196 standard. Using this standard, the apparent viscosity may be determined as:

$$V=fs,$$

where, V is the viscosity of the sample in centipoises (mPa s), f is the scale factor furnished with the instrument, and s is the scale reading of the viscometer.

In one embodiment, a suitable ultrasound transmission lotion-like oil-based transmission medium may have a viscosity between 5,000 to 2,000,000 centipoises. In another embodiment the viscosity may be between 20,000 and 2,000,000 centipoises. In yet another embodiment, a suitable ultrasound transmission lotion oil based transmission medium has a viscosity between 100,000 and 2,000,000 centipoises.

Oil based transmission mediums having a balm-like consistency can be characterized by melting point and consistency. The melting point can be determined using the standard ASTM D-127. In one embodiment, the final melting point of the composition is preferably between 50°-75° C. The standard ASTM D-127 determines the drop melting point of the petroleum wax. According to this standard, specimens are deposited onto thermometer bulbs by dipping chilled thermometers into the sample of the material. The thermometers bearing the specimens are then placed in test tubes and heated by means of a water bath until the specimen melts and the first drop falls from each thermometer bulb. The average of the temperatures which these drops fall is the drop melting point of the sample.

Consistency of an oil-based transmission medium may be characterized by cone penetration according to standard ASTM D-937, measured with a standard cone. The unit for the cone penetration is recorded in 0.1 millimeter. The cone penetration for a balm-like oil based transmission medium of the present invention may be between 30-240 and preferably between 50-200. In yet another embodiment, the cone penetration is between 60-120. Cone penetration measurement according to ASTM D-937 involves melting the sample, heating the sample to 82° C. and then cooling the sample under controlled conditions to 25° C. Penetration of the samples is then measured with a cone of standard dimensions. While at the desired temperature, a Penetrometer is used to apply the standard dimension cone to the sample for five seconds under a load of 150 grams. The depth of the penetration of the cone is used as a measure of the sample consistency.

In one embodiment, an oil based transmission medium of the present invention may be implemented using commercial products. These commercial products include lip balm, lip stick, Vaseline, petroleum and other similar products.

Gel Pad with Membrane Layer

In one embodiment, the transmission medium may be implemented as a gel pad having a membrane layer. A gel pad can be used to transmit the ultrasonic frequency signal between the ultrasonic monitor and the subject. The gel pad may be in contact with an adhesive member, an oil based transmission medium, the subject, ultrasonic monitor transducers, or a surface of a protective material that is directly or indirectly in contact with the transducers, such as an protective layer (discussed in more detail below). Gels having high oil content are generally transparent to ultrasound. Thus, the energy loss during transmission is minimized significantly. This allows the ultrasonic monitor to effectively measure both the blood flow rate and cardiac output accurately.

In one embodiment, the gel pad may be implemented as a gel pouch. FIG. 10A illustrates one embodiment of a gel pouch. Gel pouch 1060 includes a gel layer 1062, primer layers 1064 and 1066, membrane layers 1068 and 1070, and adhesive layers 1072 and 1074. The gel layer 1062 is the primary transmitting medium of the gel pouch. The primer layer can be applied to the surface of the gel layer. In an embodiment wherein the gel layer is generally shaped to have a top and bottom surface, a primer layer may be applied as an upper primer layer 1064 and/or a lower primer layer 1066. A membrane layer is attached to the gel layer via the primer layer. The membrane layer serves to aid in the handling of softer gels and prevents diluents from making contact with the subject's skin. Upper membrane layer 1068 is attached to upper primer layer 1064 and lower membrane layer 1070 is attached do lower primer layer 1066. The membrane layer can be applied to one or more surfaces of the gel layer. An adhesive layer may then be applied to the outer surface of the membrane layer. The adhesive is used to attach the gel pouch to the subject's skin, the transducer, or a protective material such as an RTV element in contact with the transducer. The adhesive may also eliminate any air pockets that may exist between the gel pouch and other surfaces. An upper adhesive layer 1072 may be applied to upper membrane layer 1068 and a lower adhesive layer 1074 may be applied to lower membrane layer 1070.

Several types of materials can be used in constructing the gel pad of the present invention. The gel layer of the gel pad (gel 1062 of FIG. 10A) may be constructed of thermoplastic gel, themoset gel, hydrogels, or other similar materials. A thermoplastic gel is generally made of a thermoplastic elastomer with a large proportion of interdispersed diluent. Thermoplastic elastomers include block copolymers such as styrene-butadiene-styrene, styrene-isoprene-styrene, styrene/ethylene-co-butylenes/styrene, and styrene/ethylene-co-propylene/styrene. The styrene end blocks form glassy domains at room temperature. The glassy domains act as physical crosslinks that provide the elastomeric properties of the polymer. During heating above the glass transition temperature of styrene, i.e., about 100° C., the glassy domains melt and the polymers revert to a liquid state. During cooling, the glassy domains re-form again. Hence, the process is reversible. Other block copolymers, such as ethylene-(ethylene-co-butylene)-ethylene copolymers which contains crystalline polyethylene end blocks, can also be used to prepare thermoplastic gels.

A thermoset gel, such as a polyurethane or silicon gel, is generally made of a chemically bonded three-dimensional elastomeric network which entraps a large amount of low volatility liquids or diluents. The elastomeric network is permanent and cannot be reversed to a liquid state through heating. A certain amount of diluent is necessary in order to ensure good conformability of the gel to the skin and low attenuation for ultrasound transmission while still maintaining the load bearing properties. The gel can be used at a temperature that ranges from −30° C. to +70° C., wherein the gel maintains its shape and load-bearing elastic properties.

Thermoset and thermoplastic gels invariably contain a large percentage of diluents entrapped in an elastomeric network. When properly formulated, these gels are stable and can resist stress or temperature cycling. The stability is governed by thermodynamic factors such as the crosslink density of the elastomeric network and the compatibility of the diluents with the elastomeric network. However, even with a thermodynamically stable gel, when brought in contact with skin, the diluents in the gel can still diffuse out and enter the living subject. This is due to the fact that there is a concentration gradient of the diluents across the skin; the natural tendency for the diluents is to migrate out of the gel, where the concentration of the diluents is high, and into skin, where the initial concentration of diluents is zero. The diffusion is thus kinetically controlled by the Fick's Law. The diffusion of diluents, particularly silicone oil, may have a deleterious effect to the living. In one embodiment, the diffusion of the diluents is prevented by adhering or laminating a compliable barrier membrane to the gel layer.

Hydrogels can consist of a water soluble polymer such as polyacrylic acid, polyacrylamide, poly (acrylic acid-co-acrylonitrile), poly(acrylamide-co-acrylonitrile), etc. They are dissolved in a large amount of water, approximately 50% to 98% by weight of the total mixture. The mixtures are optionally thickened by ions such as sodium, zinc, calcium, etc., which are provided by adding the corresponding metal salts. When used with a membrane, the membrane can effectively seal the mixtures to prevent the water evaporation or migration.

The membrane layer may be made of a thin film of polyurethane, silicone, poly(vinyl chloride), natural or synthetic rubbers, polyester, polyamides, or polyolefins which include low density polyethylene, plastomers, metallocene olefin copolymers, or other similar materials. In fact, any thin polymer film that is pliable and conformable is within the scope of this invention. Those skilled in the art can determine a suitable membrane material depending on the gel material selected. The membrane can be laminated to the gel pad using an adhesive. The membrane can also be formed by spraying of coating a film forming liquid such as a polyurethane elastomer solution, or latex onto the surfaces of the gel layer. Upon drying of the liquid, a thin membrane is formed which can achieve the same result as the laminating process. Depending on the type of diluents in the gel layer, a membrane is selected to give the best barrier effect. The membrane is preferably as thin and soft as possible so that it complies to the skin well and minimizes the possibility of air entrapment. The membrane also provides for easier gel pad handling, reduced dirt accumulation, and easier cleaning.

Several types of adhesives and primers may be used to generate the gel pouch of FIG. 10A. For example, Automix™ Polyolefin Adhesion Promoter 05907 by 3M™ and LOCTITE™ 770 Polyolefin Primer by Loctite can be used as a primer between the gel layer and membrane layer. AROSET™ 3250 pressure sensitive adhesive by Ashland Specialty Chemical Company can be used as the adhesive between a membrane layer and the subject's skin. DOW CORNING 7657 Adhesive used with SYL-OFF 4000 Catalyst by Dow Corning™ may be used as an adhesive between the membrane layer and an RTV element.

The pressure sensitive adhesive applied to the outer surface of the membrane layer can be rubber, silicone or acrylic based depending on the based material of the gel. For example, if thermoplastic gel is used, a rubber based pressure sensitive adhesive will provide better adhesion. It is also preferable that the pressure sensitive adhesive is medical grade that does not cause skin sensitization. If a membrane is in direct contact with the skin, it is also desirable that the membrane itself does not cause skin sensitization. Some membrane materials made of natural rubber latex are known to cause allergic reaction to the skin of some people.

In another embodiment, the gel pad may consist of a single layer of thermoplastic gel material. This is particularly convenient if a biocompatible fluid such as medical grade mineral oil is used as the diluent in the gel. Such oil, if migrates into the skin, does not cause adverse effect to the living tissues. For example, baby oil, a medical grade mineral oil, may be used for the diluent. In this case, the thermoplastic gel material is compliant enough to the surface of the subject such that no adhesive is needed between the gel pad and the subject's skin. In particular, when applied with a slight amount of pressure, such as that applied by a wrist-worn ultrasonic monitor with a wrist-strap, any existing air pockets are generally eliminated. Minimum adhesion is required to keep the single layer thermoplastic gel pad in place when in contact with the ultrasonic monitor and a subject's skin. This is advantageous because it is simple, inexpensive to construct and allows a large number of adhesives to be used to keep the gel pad in contact with a protective layer, such as RTV material. In one embodiment, the gel may have a thickness of between about 1 and 10 millimeters. In some embodiments, the gel may have a thickness between 1 and 5 millimeters.

Adhesive Member

An adhesive member may adhere a surface of the ultrasonic monitor or transmission medium to a user or other subject to be monitored. In one embodiment, a first surface of the adhesive member is attached to a surface of the transmission medium. A second surface of the adhesive member may be attached to the user (for example, the user's skin).

An adhesive member may be implemented as a double-sided tape. A double sided tape may include a generally flat layer of polymeric material with an adhesive on both surfaces. The polymeric material can include a plastic film, elastomeric film, gel layer, adhesive layer, or a hydrocolloid substance. In one embodiment, the polymeric material is as thin as possible to minimize the attenuation to the ultrasound. If the polymeric material is an elastomer, gel, adhesive or hydrocolloid, the adhesion on both surfaces can be achieved by adjusting the softness and surface tack in the formulation. No additional adhesive coating on the surfaces is required. The thickness of an adhesive member may vary depending on the application. An example of a thickness range suitable for wrist-worn ultrasonic monitors is from 0.5 to 5 millimeters.

When subjected to a vibration such as ultrasound, polymeric materials may transmit some energy and dissipate some energy as heat. The energy loss by heat dissipation is called damping. The power reduction in an ultrasound transmission signal due to damping is called attenuation. The degree of damping with a given polymeric material depends on the vibration frequency of the received signal and temperature of the polymeric material. A preferred polymeric material can be selected such that it maximizes the energy transmission while minimizes the energy dissipation. In one embodiment, factors that can be considered in selecting an appropriate polymeric material may include the applied ultrasound frequency and the applied temperature of the ultrasound monitor. For ultrasonic monitor applications, the applied ultrasonic frequency may be between as 30 kHz to 30 MHz. The applied temperature of the ultrasonic monitor may be the ambient temperature of the subject's skin. Those skilled in the art can select a suitable material which minimizes the vibration damping of a polymeric material.

FIGS. 10B-10C illustrate an embodiment of an adhesive member. Adhesive member 1080 of FIG. 10B includes a middle layer 1084, an upper adhesive layer 1082 and a lower adhesive layer 1086. Middle layer 1084 may be implemented as a polymeric material as discussed above, or some other suitable material. Upper adhesive layer 1082 and lower adhesive layer 1086 may be implemented as an adhesive as discussed herein. FIG. 10C illustrates a side view of adhesive member 1080 of FIG. 10B. Adhesive layer 1090 of FIG. 10C illustrates middle layer 1084 as considerably thicker than upper adhesive layer 1082 and lower adhesive layer 1086. FIGS. 10B-10C illustrate only an example of an adhesive member. Other adhesive members can be implemented having layers proportions that differ from that illustrated in FIGS. 10B-10C.

In one embodiment, the double-sided tape of the present invention may be implemented as a pressure sensitive adhesive in the form of transfer tape. Transfer tape is an adhesive layer protected on both sides by a release paper. An ultrasonic monitor user can peel off a release paper from one side to adhere to the heart rate monitor and then remove the release paper from the other side to adhere the other side of the transfer tape to the user. An example of a suitable transfer tape is AveryDennison MED 1136.

A polymeric material implemented as a plastic film can include polyester, NYLON (polyamide), polyethylene, polypropylene, poly(vinyl chloride), poly(ethylene-co-vinyl acetate), TEFLON, and other similar materials. The plastic film can be coated with a pressure sensitive adhesive on each side. The pressure sensitive adhesive may secure the monitor to the subject to provide intimate contact between the two. In one embodiment, the pressure sensitive adhesive can be biocompatible so that it will not cause skin sensitivity in a subject. Suitable pressure sensitive adhesives may be acrylic or rubber based. A commercial double-sided tape such as 3M's SCOTCH tape is an example of a suitable acrylic double sided tape.

In one embodiment, the surfaces of an adhesive member may have the same or different pressure sensitive adhesives. When one side of the adhesive member will adhere to the ultrasound transducer and the other side to a subject, a pressure sensitive adhesive with higher adhesion may be used for the transducer side and a pressure sensitive adhesive with a lower adhesion may be used on the subject side. This differing adhesion approach may help in maintaining the adhesive against the ultrasonic monitor while not damaging or removing skin from a subject after the monitor is pulled away from the subject.

A polymeric material comprised of an elastomeric film can be a natural or synthetic rubber. Examples of elastomeric films suitable for user include as polyurethane, polychloroprene (Neoprene), and polyisobutylene (Butyl rubber). In one embodiment, the elastomeric film may be made of a natural rubber latex. In some embodiments, the elastomeric film is made of a thermoplastic elastomer (TPE) such as KRATON polymers or a thermoplastic rubber vulcanizate (TPV), such as SANTOPRENE. TPEs and TPVs are elastomeric materials that can be processed like a thermoplastic and offer cost advantages.

An elastomeric film can be coated with a pressure sensitive adhesive, similar to that used with the plastic films. One example of such an elastomeric film is AveryDennison MED 5020, which is a 1-millimeter thick polyurethane film coated on one side with a non-sensitizing pressure sensitive adhesive. The MED 5020 can be coated with a pressure sensitive adhesive on the other side to make a double-sided tape.

The polymeric material can also be a softer material, such as gel, adhesive, mastic or hydrocolloid. A gel material can be similar to that described herein or in U.S. Pat. No. 6,843,771. The adhesive layer used for the gel can be either a hot melt adhesive or a mastic.

A mastic is a class of sealant that is pliable, stretchable and has some degree of surface tack. It has a consistency similar to a chewing gum so that it maintains its shape at ambient temperature. However, contrary to a chewing gum with its surface dusted with powder to render it non-tacky, a mastic has tacky surfaces.

The hydrocolloid materials are similar to those provided by AveryDennison such as MED 2190H and MED 2191H. All these materials, due to their softness, may have some degree of tackiness by themselves. Tackiness refers to the feel of stickiness without leaving any residue when quickly touch with a finger. An ASTM standard D3121-99(Standard Test Method for Tack of Pressure-Sensitive Adhesives by Rolling Ball) can be used to quantitatively measure tackiness of pressure sensitive adhesives or mastics with a stainless rolling ball. In ASTM D3121, a sample of adhesive is placed over an inclined trough and adjacent horizontal surface. A steel ball is placed on the adhesive at the top of the trough. The ball is allowed to roll down the inclined trough and onto the horizontal surface covered by the adhesive. A measure of tack is taken as the distance the ball travels on the adhesive. In some embodiments, a pressure sensitive adhesive can be formulated with a tackifier in the layer. This promotes tackiness and renders the adhesive suitable for use in the present invention. In this case, the pressure sensitive adhesive surfaces do not have to be coated with additional adhesive or other materials.

FIG. 11A illustrates a top view of one embodiment of a transmission medium component 1180. Transmission medium component 1180 may be implemented as gel pad having a membrane, an oil-based transmission medium, an adhesive member, a combination of these, or some other material. Transmission medium component 1180 includes transmission medium 1182, first cover 1184 and second cover 1186. FIG. 11B illustrates a side view of transmission medium component 1180. In the embodiment illustrated, transmission medium 1182 has a flat disk-like shape. In some embodiment, transmission medium 1182 may have a rectangular shape, cylindrical shape, or some other shape. The covers are applied to the transmission medium during manufacturing and protect it until it is used. The covers can be constructed of wax paper or some other type of material.

Covers 1184 and 1186 are removed before use of transmission medium 1182. Transmission medium 1182 is then applied to the area between the ultrasonic monitor and the subject's skin. In one embodiment, wherein the monitor is worn on the wrist, transmission medium 1182 is applied between the wrist worn monitor and the subject's wrist. In one embodiment, the monitor includes a recess constructed in its outer surface that is positioned towards the subject. Transmission medium 1182 can be applied to the recessed area on the monitor to help keep it in place. When transmission medium 1182 includes a pressure sensitive adhesive and is compressed between the monitor and the subject, it may adhere to both the monitor and the subject. Transmission medium 1182 may be compressed when the monitor is strapped to a subject, held in place without a strap for a period of time, or in some other manner that straps, fastens or otherwise applies the monitor to the subject.

Figure 12A:
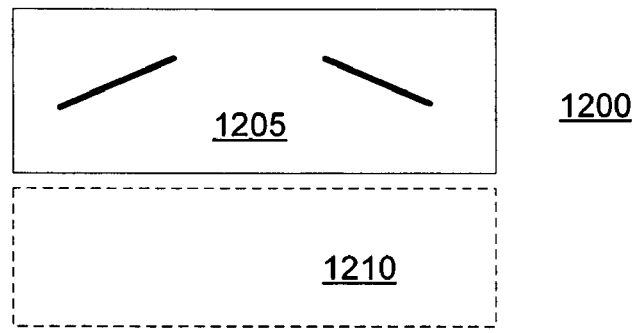
FIG. 12A illustrates one embodiment of a transmission medium configuration.
Figure 12B:
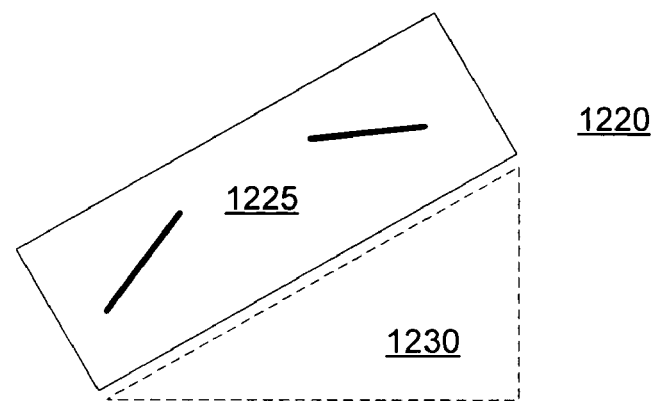
FIG. 12B illustrates one embodiment of a transmission medium configuration.
Figure 12C:
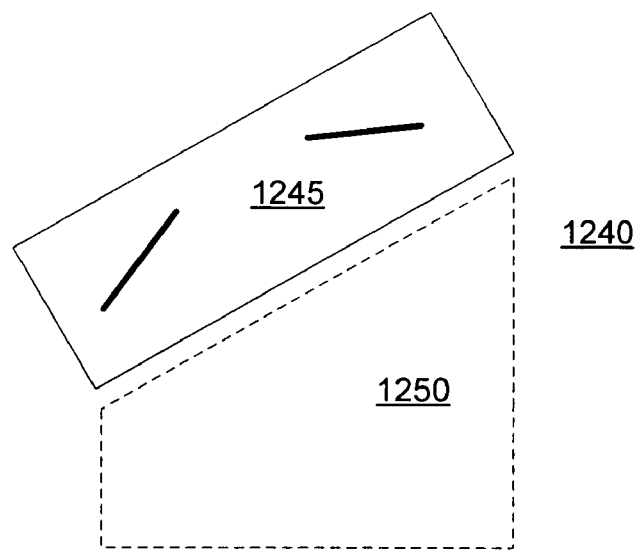
FIG. 12C illustrates one embodiment of a transmission medium configuration.

The transmission medium shape and thickness can be designed to allow ultrasonic monitors to operate at different bias angles. Ultrasonic monitor 1200 of FIG. 12A illustrates a monitor module 1205 in contact with a transmission medium 1210 having a rectangular cross section. Ultrasonic monitor 1220 of FIG. 12B illustrates a monitor module 1225 in contact with transmission medium 1230 having a triangular cross section. Ultrasonic monitor 1240 of FIG. 12C illustrates a monitor module 1245 in contact with transmission medium 1240 and FIG. 12C having a trapezoidal cross section. Transmission mediums 1210, 1230 and 1240 may be comprised of a gel having a membrane layer, an oil-based gel, or some other material. The dimensions of these transmission medium shapes are based on the desired bias angle and the depth of the moving object to be detected.

The transmission medium may be used with an ultrasonic monitor in several ways. In one embodiment, a transmission medium can be heated to a molten state and over-molded onto the transducer or the plastic housing of the ultrasonic monitor. Oil-based transmission media having a fixed or balm-like consistency are well suited for over-molding. Though the oil-based transmission medium will adhere to the transducer or the plastic housing, an encapsulant may be used to ensure a durable bond onto the transducer, and then the oil-based transmission medium is applied on the surface of the encapsulant. Encapsulants suitable for over-molding include EC6000 by ECLECTRIC PRODUCTS, Inc.

In another embodiment, a protective layer may be positioned between the transducers and the transmission medium. The transmission medium is positioned between the protective layer and the subject. The protective layer may be molded such that it encompasses the transducers and a portion of the PCB outer surface. In one embodiment, the mold is mounted to the PCB. The protective layer material is then placed into the mold. Though the protective layer will adhere to the exposed PCB surface within the mold, an adhesive may be used to further secure the protective layer material to the PCB. A suitable protective layer material can provide excellent ultrasonic signal transmission and is firmer than a natural oil-based transmission medium. The firmness of the suitable protective layer material can prevent damage to the transducer elements due to contact from the oil-based transmission medium and other objects.

In one embodiment, the protective layer may be comprised of a room temperature vulcanizing (RTV) silicone rubber layer adhesive. RTV silicones, which are used to encapsulate and protect transducers, can be substituted with other types of materials so long as they provide adequate mechanical strength, exhibit minimum impedance to ultrasound, and can be applied easily and with the least entrapped air bubbles. Suitable substitutes for RTV silicones may be materials such as include flexible epoxy, elastomeric polyurethane, flexible acrylic, etc. RTV silicone substitutes can be single or two component systems. These substitutes are preferably applicable as solvent-free liquids, and can be crosslinked at room temperature without using heat. The crosslinking can be achieved by chemical reactions, moisture cured mechanisms, or ultra violet light. An example of a suitable RTV replacement material may include Eccobond 45 with catalyte 15, provided by Emerson Cuming of Billerica, Mass. Eccobond 45 with Catalyst 15 is a black, filled epoxy adhesive which, by varying the amount of catalyst used, can adjust the hardness from flexible to rigid. It has an easy mix ratio range and bonds well to a wide variety of substrates. Other examples of RTV substitute materials may include Stycast U2516HTR (a flexible polyurethane casting resin) and Stycast 1365-65N (a flexible epoxy "gel" encapsulant), also provided by Emerson Cuming.

Figure 13A:
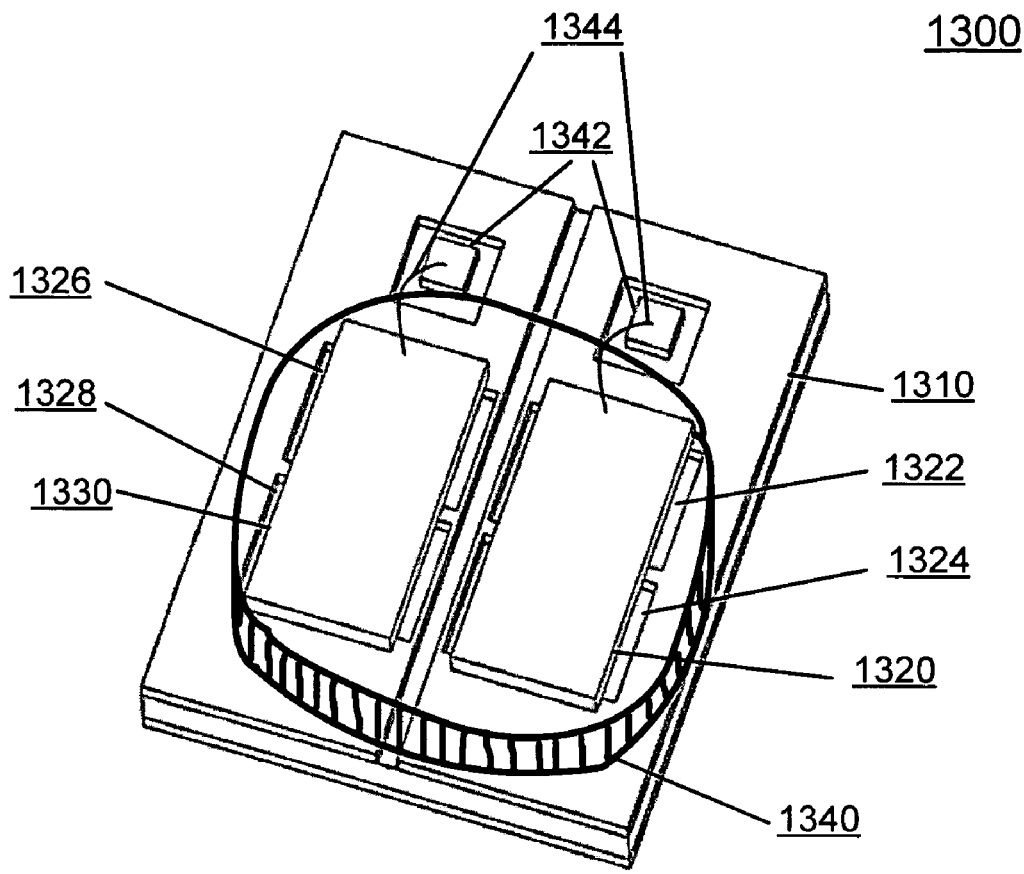
FIG. 13A illustrates one embodiment of a perspective view of an ultrasonic monitor on a PCB with a mold.
Figure 13B:
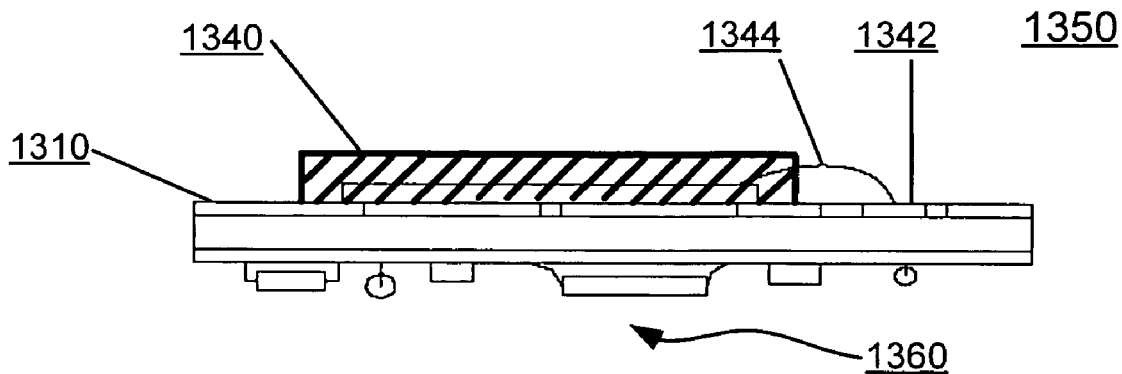
FIG. 13B illustrates one embodiment of a side view of an ultrasonic monitor on a PCB with a mold.

An embodiment of a PCB system that incorporates a molded protective layer is shown in FIGS. 13A and 13B. The monitor of system 1300 in FIG. 13A includes an outer layer 1310 of a PCB, transducers 1320 and 1330 mounted to the outer layer, protective layer mold 1340, copper contact points 1342, connecting wires 1344 that connect copper contact points 1342 to transducers 1320 and 1330, air gap portions 1322 and 1324 underneath transducer 1320 and air gap portions 1326 and 1328 underneath transducer 1330. FIG. 13B illustrates a side view of the PCB system and further illustrates circuitry 1360 used to implement the monitor that is mounted to the opposite surface of the transducers. Protective layer mold 1340 is constructed such that it encompasses the transducers, air gap portions, and a portion of the outer layer of the PCB. When the protective layer is poured, injected or otherwise placed within mold 1340, the protective layer will cover the transducers, air gap portions and the portion of the outer layer of the PCB encompassed by mold 1340. Connecting wires 1344 may be located over or under mold 1340. Mold 1340 may be implemented as a solder mold and attached to the PCB using appropriate adhesives as discussed above. The protective material is placed into mold 1340 during production. The oil-based transmission media may then be attached to the protective material layer using an appropriate adhesive.

The protective material can be selected such that it acts as a mechanical isolator between the transducers and outside forces. The protective material absorbs outside forces, such as contact or pressure from a subject's skin, and prevents them from affecting the resonating frequency of the transducers. A protective material formed of RTV may be constructed from several types of materials, including Silastic™ E RTV Silicone Rubber and DOW CORNING 3110, 3112 and 3120 RTV rubbers, all by DOW CORNING™. DOW CORNING™ 1301 primer and other similar primers may be used to attach the RTV material to the PCB.

Encapsulated Ultrasonic Monitor

In one embodiment of the present invention, the ultrasonic monitor can be encapsulated to make it water resistant. The ultrasonic monitor can be sealed using an ABS plastic material, gel material, or both. For instance, the electronic component side can be sealed in a plastic material such as ABS while the transducer side is sealed by a softer gel material such as a natural oil-based transmission medium. Oil-based transmission media having a fixed or balm-like consistency are well suited for over-molding. In another embodiment, both the transducer side and the electronic component side can be sealed using an ABS plastic material.

In some embodiments, the sealed assembly can be formed with a recessed portion located over the transducers or an protective layer portion of the ultrasonic monitor. An oil-based transmission medium may be positioned at the recessed area to provide ultrasonic signal transmission. Placing the oil-based transmission medium at the recessed portion will help maintain the position of the oil-based transmission medium at the location of the recessed portion and over the transducers. The transmission medium illustrated and discussed in reference to FIGS. 11A-B can be used in this embodiment. In some embodiments, the resulting assembly can be further molded or mechanically coupled in some way to a polyurethane based wristwatch strap. Both final assemblies will be waterproof and retain good ultrasonic transmission properties with a subject.

Figure 14A:
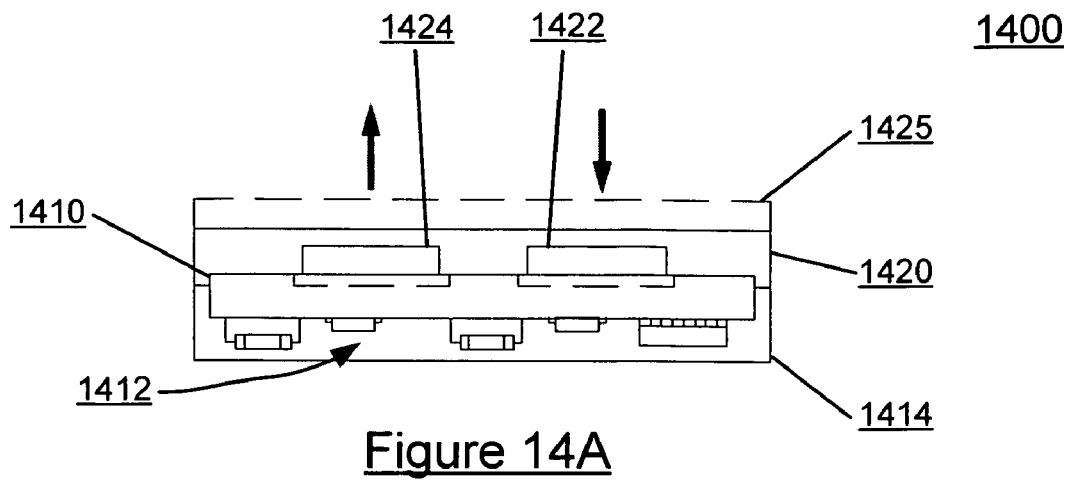
FIG. 14A illustrates one embodiment of a side view of an encapsulated PCB board.

FIG. 14A illustrates an embodiment of a sealed ultrasonic monitor 1400. Monitor 1400 includes PCB 1410, circuitry 1412, plastic housing 1414, protective layer 1420, transducers 1422 and 1424 and transmission medium 1425. In one embodiment, protective layer 1420 may include RTV silicone rubber or a suitable replacement material, epoxy, or a combination of these materials. PCB 1410 and circuitry 1412 are molded and sealed in plastic (such as ABS plastic) housing 1414. Protective layer 1420 is molded or cast over the transducers and sealed against the plastic housing. Transmission medium 1425 is then positioned over protective layer 1420.

Figure 14B:
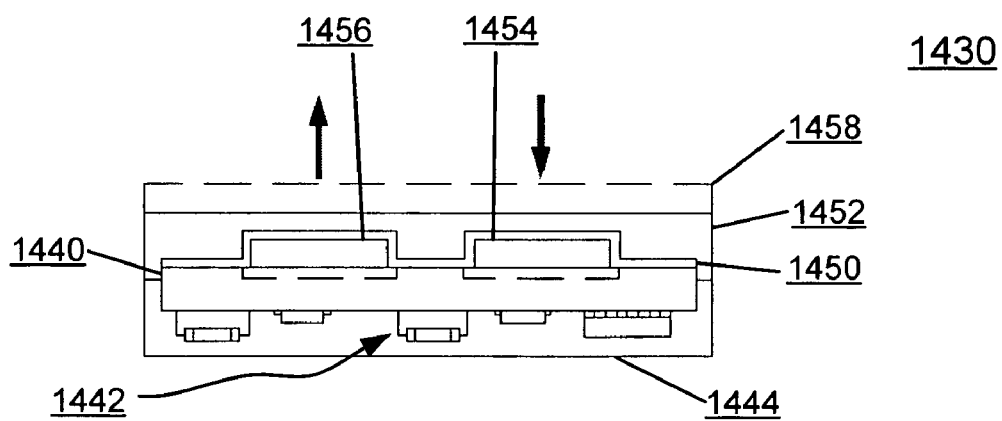
FIG. 14B illustrates one embodiment of a side view of an encapsulated PCB board.

FIG. 14B illustrates an embodiment of a sealed ultrasonic monitor 1430. Monitor 1430 includes PCB 1440, circuitry 1442, plastic housing 1444, adhesive layer 1450, protective layer 1452, transducers 1454 and 1456 and transmission medium 1458. Monitor 1430 is similar to monitor 1400 except that adhesive layer 1450 is applied between protective layer 1452 and transducers 1454 and 1456 and PCB 1440.

Figure 14C:
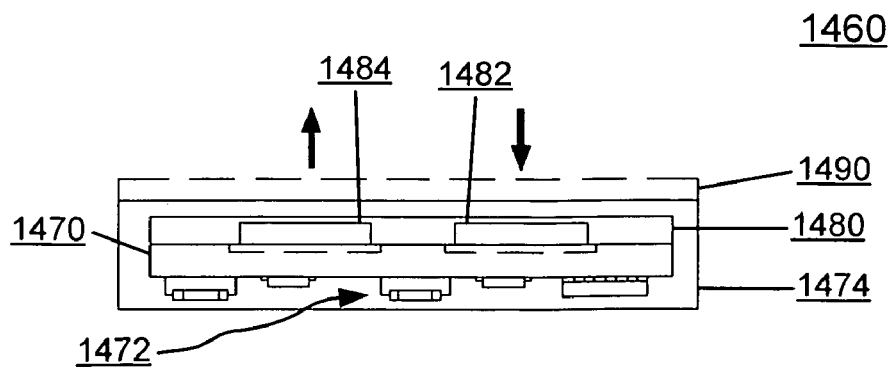
FIG. 14C illustrates one embodiment of a side view of an encapsulated PCB board.

FIG. 14C illustrates an embodiment of a sealed ultrasonic monitor 1460. Monitor 1460 includes PCB 1470, circuitry 1472, plastic housing 1474, protective layer 1480, transducers 1482 and 1484 and transmission medium 1490. Protective layer 1480 is applied over transducers 1482 and 1484. Plastic housing 1474 encapsulates the entire ultrasonic monitor, including protective layer 1480, PCB 1470 and circuitry 1472. Transmission medium 1490 is in contact with a surface of plastic housing 1474 closest to transducers 1482 and 1484.

Figure 15A:
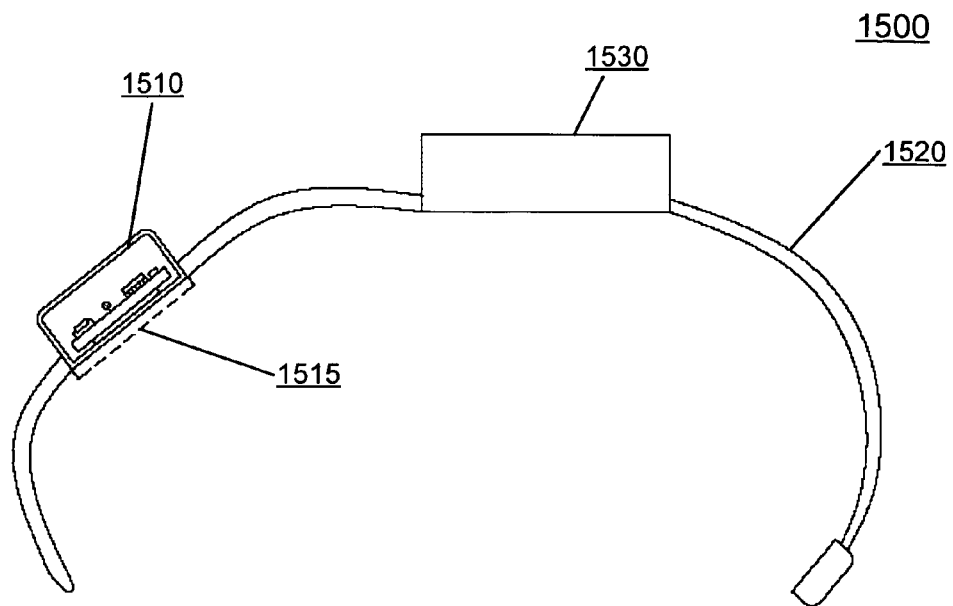
FIG. 15A illustrates an embodiment of an ultrasonic monitor system with an encapsulated transmission medium.

An encapsulated ultrasonic monitor may be used with a permanently attached or disposable transmission medium. The transmission medium may be oil based, a gel pad, or a combination of the two. The disposable transmission media can be attached on a recessed area of a surface of the ultrasonic monitor. An embodiment of a wrist worn ultrasonic monitor 1500 that is encapsulated in a housing is illustrated in FIG. 15A. Monitor 1500 includes ultrasonic monitor module 1510, transmission medium 1515 attached to ultrasonic monitor module 1510, display device 1530, and strap 1520 attached to the display device and monitor module. Transmission medium 1515 is attached to ultrasonic monitor module 1510 during production. In one embodiment, the transmission medium can be attached to the monitor module 1510 though a molding process. Fixed or balm-like consistency biocompatible oil based transmission mediums are well suited for attachment to ultrasonic monitor module 1510.

Figure 15B:
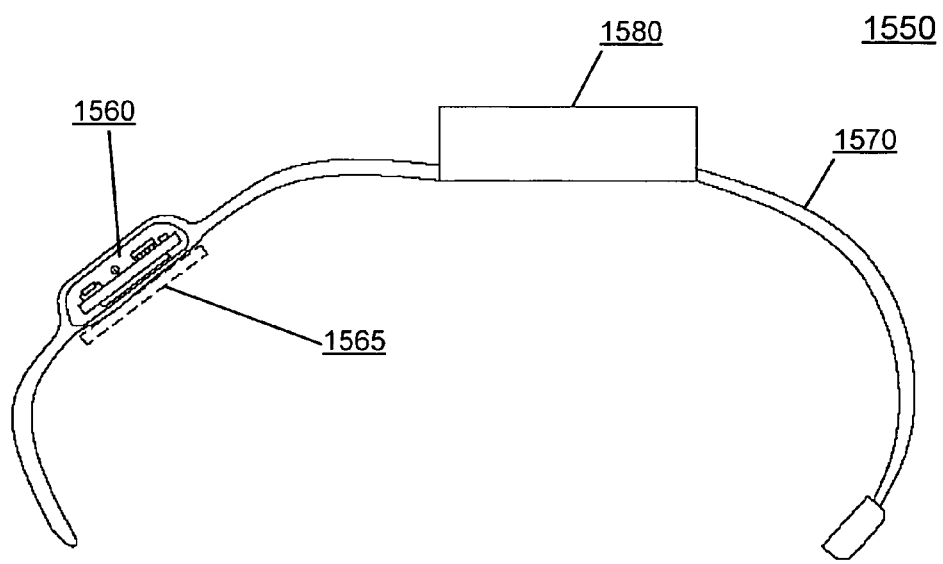
FIG. 15B illustrates an embodiment of an ultrasonic monitor system with an attached transmission medium.

One embodiment of a wrist worn ultrasonic monitor 1580 that is encapsulated in a housing is illustrated in FIG. 15B. Monitor 1580 includes ultrasonic monitor module 1560, disposable transmission medium 1565 attached to monitor module 1560, display device 1580, and strap 1570 attached to the display device and monitor module. The disposable transmission medium 1565 can be attached to the monitor module just before the monitor is used. Fixed or balm-like consistency biocompatible oil based transmission media are well suited for use as disposable transmission medium 1565. Ultrasonic monitor modules 1510 and 1560 contain slightly different shapes. This is for purposes of example only. The shapes of ultrasonic monitor modules of FIGS. 15A and 15B are interchangeable and are not intended to limit the scope of the present invention.

The foregoing detailed description of the invention has been presented for purposes of illustration and description. It is not intended to be exhaustive or to limit the invention to the precise form disclosed. Many modifications and variations are possible in light of the above teaching. The described embodiments were chosen in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

We claim:

1. A method for determining a heart rate, comprising:
   transmitting a continuous signal towards a subject's artery for an initial period of time;
   using a microcontroller, determining an initial heart rate of the subject from a reflected continuous signal received during the initial period of time;
   using the microcontroller, determining a duration of a subsequent period of time based on the initial heart rate;
   transmitting a non-continuous signal towards the artery during the subsequent period of time after the initial period of time;
   using the microcontroller, determining the subsequent heart rate of the subject from a reflected non-continuous signal; and
   using the microcontroller, determining the subject's initial heart rate is not associated with strenuous activity by the subject, the transmitting the non-continuous signal is responsive to the determining the subject's initial heart rate is not associated with strenuous activity by the subject.

2. The method of claim 1, wherein the initial period of time corresponds to between three to five heart beats of the subject.

3. The method of claim 1, wherein said determining the duration includes:
   determining a window of time associated with an expected heart beat.

4. The method of claim 3, wherein the expected heart beat is a next occurring heart beat.

5. The method of claim 3, wherein the expected heart beat is after a next occurring heart beat.

6. The method of claim 1, wherein said step of transmitting a non-continuous signal includes:
   determining a heart rate period between two previous heart beats of the subject;
   terminating power to a transmitting device for a period of time comprising a majority of the heart rate period; and
   providing power to the transmitting device for the remainder of the heart rate period after the majority of the heart rate period has transpired.

7. The method of claim 6, wherein said step of terminating power includes:
   terminating power to the transmitting device for seven eighths of the heart rate period.

8. The method of claim 1, wherein said step of transmitting a non-continuous signal includes:
   not providing a signal towards the subject's artery for a first time period which includes at least one heart beat; and
   providing a signal towards the subject's artery during a second time period associated with an expected heart beat.

9. The method of claim 1, further comprising:
   determining the subject's heart rate is stable for two or more heart beats after the initial period, the transmitting the non-continuous signal is responsive to the determining the subject's heart rate is stable.

10. One or more processor readable storage devices having processor readable code embodied on said processor readable storage devices, said processor readable code for programming one or more processors to perform a method comprising:
    driving a transmitter device continuously for an initial period of time, the transmitter device configured to transmit a signal to a subject when driven;
    detecting a heart rate for the subject from a reflected signal during the initial period of time; and
    driving the transmitter device non-continuously for a second period of time in response to detecting the heart rate;
    said step of driving the transmitter device non-continuously includes determining the subject is not exercising and, in response to the determining, preventing driving of the transmitter device.

11. The one or more processor readable storage devices of claim 10, wherein the initial period of time is associated with at least two heart beats.

12. The one or more processor readable storage devices of claim 10, wherein said step of driving the transmitter device non-continuously includes:
   driving the transmitter device in response to determining a heart beat of the subject is expected to occur.

13. The one or more processor readable storage devices of claim 10, wherein said step of driving the transmitter device non-continuously includes:
   terminating power to the transmitter device in response to said step of detecting the heart rate;
   determining a heart beat is expected to occur; and
   providing power to the transmitter device in response to said step of determining the heart beat is expected to occur.

14. The one or more processor readable storage devices of claim 10, wherein said step of driving the transmitter device non-continuously includes:
   determining the subject's heart rate has been stable for a period of time; and
   preventing driving of the transmitter device during a next occurring heart beat of the subject in response to the determining the subject's heart rate has been stable.

15. A heart rate monitor, comprising:
   a transmitter device that transmits a signal towards a subject;
   a receiver device, said receiver device detects a reflected signal;
   a driving circuit in communication with said transmitter device and said receiver device, the driving circuit drives the transmitter device at full power and at reduced power in response to detecting a heart rate of the subject, said driving circuit includes a timer configured to be set to expire in a period of time derived from the subject's heart rate; and
   signal processing circuitry connected to the signal receiver.

16. The heart rate monitor of claim 15, wherein said driving circuit drives the transmitter device for an initial period of time at full power before driving the transmitter device at the reduced power.

17. The heart rate monitor of claim 15, wherein said driving circuit drives the transmitter device at the reduced power during the period of time, which is between two or more consecutive heart beats.

18. The heart rate monitor of claim 15, further comprising:
   a microcontroller which enters an idle state while said driving circuit drives said transmitter device at the reduced power.

19. The heart rate monitor of claim 15, wherein the transmitter device comprises a transducer.

20. A heart rate monitor, comprising:
   a transmitting element that transmits a signal towards a subject's artery;
   a receiving element which receives a reflected signal from the subject's artery;
   signal processing circuitry in communication with said receiving element, said signal processing circuitry determines a heart rate of the subject from the reflected signal and determines a number of heart beats for which the heart rate has been stable; and
   a driving circuit in communication with said transmitting element, said receiving element and said signal processing circuitry, the driving circuit driving the transmitting element at full power for an initial period of time, and alternately driving the transmitting element at full power and low power for a subsequent period of time in response to the determined heart rate, the signal processing circuitry determines the subsequent period of time based on the determined number of heart beats.

21. The heart rate monitor of claim 20, wherein the signal processing circuitry determines a period of time for which said driving circuit drives the transmitting element at the low power.

22. The heart rate monitor of claim 21, wherein the signal processing circuitry determines the subsequent period of time based on an initial heart rate of the subject.

23. The heart rate monitor of claim 20, wherein the heart rate monitor is a wrist worn device.

24. A heart rate monitor, comprising:
   a transmitting element that transmits a signal towards a subject's artery;
   a receiving element which receives a reflected signal from the subject's artery;
   signal processing circuitry in communication with said receiving element, said signal processing circuitry determines a heart rate of the subject from the reflected signal; and
   a driving circuit in communication with said transmitting element, said receiving element and said signal processing circuitry, the driving circuit drives the transmitting element at full power for an initial period of time, and alternately drives the transmitting element at full power and low power for a subsequent period of time in response to the heart rate determined by the signal processing circuitry;
   the signal processing circuitry determines the subsequent period of time based on a range of the subject's heart rate.

25. The method of claim 1, wherein the subject is a person.

* * * * *